US009244010B2

(12) United States Patent
Wagner et al.

(10) Patent No.: US 9,244,010 B2
(45) Date of Patent: Jan. 26, 2016

(54) DEVICE AND METHOD FOR DETECTING SCATTERED LIGHT SIGNALS

(71) Applicant: AMRONA AG, Zug (CH)

(72) Inventors: Ernst Werner Wagner, Winsen (DE); Andreas Siemens, Laatzen (DE)

(73) Assignee: AMRONA AG, Zug (CH)

( * ) Notice: Subject to any disclaimer, the term of this patent is extended or adjusted under 35 U.S.C. 154(b) by 0 days.

(21) Appl. No.: 14/239,825

(22) PCT Filed: Sep. 6, 2013

(86) PCT No.: PCT/EP2013/068504
§ 371 (c)(1),
(2) Date: Feb. 20, 2014

(87) PCT Pub. No.: WO2014/037520
PCT Pub. Date: Mar. 13, 2014

(65) Prior Publication Data
US 2015/0204781 A1    Jul. 23, 2015

(30) Foreign Application Priority Data
Sep. 7, 2012   (EP) .................................... 12183529

(51) Int. Cl.
*G01N 21/00*    (2006.01)
*G01N 21/53*    (2006.01)
(Continued)

(52) U.S. Cl.
CPC ................ *G01N 21/53* (2013.01); *G01N 15/06* (2013.01); *G01N 15/1434* (2013.01); *G08B 17/107* (2013.01); *G08B 29/185* (2013.01); *G01N 2201/062* (2013.01)

(58) Field of Classification Search
CPC .... G08B 29/185; G08B 17/107; G01N 21/00; G01N 2201/062

USPC ......................................................... 356/342
See application file for complete search history.

(56) References Cited

U.S. PATENT DOCUMENTS 7,016,526 B2 * 3/2006 Smilansky ......... G01N 21/9501
                                                    348/126
7,471,394 B2 * 12/2008 Padmanabhan .... G01N 15/1404
                                                    356/246

(Continued)

FOREIGN PATENT DOCUMENTS

CN       1898551 A    1/2007
CN     101135653 A    3/2008
(Continued)

OTHER PUBLICATIONS

Kapila K Pahalawatta et al., "Classifying Airborne Particles", Digital Image Computing Techniques and Application (DICTA), 2011 International Conference on, IEEE, Dec. 6, 2011.

*Primary Examiner* — Roy M Punnoose
(74) *Attorney, Agent, or Firm* — Cesari and McKenna, LLP

(57) ABSTRACT

A device and a method for detecting scattered light signals is specified. A light source exposes a scattered light area in which particles may be present to light. With the objective of reducing costs and improving detection accuracy, the device comprises a plurality of optical sensors for detecting scattered light and an evaluation unit for evaluating the signals detected by the optical sensors, wherein the sensors are each arranged at a sensor angle relative to the incident axis of the incident light so as to detect scattered light from the scattered light area, wherein one of the plurality of optical sensors is a reference sensor, and wherein the evaluation unit is designed to relate the signal profiles of the other optical sensors to the signal profile of the reference sensor, wherein the signal profiles of the optical sensors serve in classifying any particles which may be present in the scattered light area.

29 Claims, 20 Drawing Sheets

(51) Int. Cl.
*G08B 17/107* (2006.01)
*G01N 15/06* (2006.01)
*G01N 15/14* (2006.01)
*G08B 29/18* (2006.01)

(56) References Cited

U.S. PATENT DOCUMENTS

| 7,630,063 | B2* | 12/2009 | Padmanabhan | G01B 11/272 356/246 |
| 9,036,150 | B2* | 5/2015 | Wedler | G01N 21/53 356/338 |
| 2005/0105077 | A1* | 5/2005 | Padmanabhan | G01B 11/272 356/39 |
| 2005/0118723 | A1* | 6/2005 | Padmanabhan | G01N 15/1459 436/164 |
| 2013/0135607 | A1* | 5/2013 | Wedler | G01N 21/53 356/51 |

FOREIGN PATENT DOCUMENTS

| EP | 1408469 | 4/2004 |
| GB | 2259763 A | 3/1993 |

* cited by examiner

US 9,244,010 B2

DEVICE AND METHOD FOR DETECTING SCATTERED LIGHT SIGNALS

CROSS REFERENCE TO RELATED APPLICATIONS

This application is the National Stage of International Application No. PCT/EP2013/068504, filed Sep. 6, 2013, which claims the benefit of European Application No. 12 183 529.2, filed Sep. 7, 2012. The contents of both applications are hereby incorporated by reference in their entirety.

BACKGROUND OF THE INVENTION

1. Field of the Invention

The present invention relates to a device as well as a method for detecting scattered light signals.

2. Background Information

Particularly in the field of fire detection devices, smoke detectors which operate on optical principles are known, whereby a scattered light area, in which particles possibly distributed in the air could be present, is subjected to light from a light source. Such particles can be caused for example by dust particles or tobacco smoke particles, but also room fires, the detecting of which is imperative. Outside of the direct optical path of the light emitted from the light source, conventional devices provide for the arranging of optical sensors such as for example photodiodes, photoresistors or the like having an correspondingly associated amplifier circuit. The sensors detect any light there may be scattered by the particles and issue an alarm signal upon for example a specific threshold being exceeded.

Furthermore, systems for classifying different types of particles are known; i.e. in particular systems for classifying different types of fire on the basis of particle properties. For example, a device is known from printed publication EP 2281 286 A1 which enables differentiating between dust particles and those particles which develop during fires. In addition to scattered light sensors (optical sensors), such conventional systems for classifying particle type usually also utilize other types of sensors—for example gas sensors or the like.

The cited conventional devices have the disadvantage of either, in the case of relatively inexpensive configuration, classification according to different kinds of particles only being unreliably possible and with no effective variable disturbance detection and/or suppression, or that relatively expensive sensor technologies need to be used such as for example gas sensors or the like. This drives up the costs and the circuit complexity.

Moreover gas sensors in particular have the disadvantage of needing relatively high energy.

The present invention is based on the objective of further developing a conventional device for detecting scattered light signals such that it can be simply and economically configured and manufactured and the detection accuracy improved. The energy consumption is additionally to be reduced.

This objective is accomplished by a device in accordance with independent claim 1 as well as a method in accordance with independent claim 24.

The dependent claims set forth advantageous further developments of the inventive solution.

The invention is based on the following basic knowledge:

The basic principle behind devices which work optically in detecting scattered light signals, particularly in smoke detectors and the like, is capitalizing on the different scattering characteristics of different types of particles distributed in the ambient air. The ambient air hereby constitutes a carrier fluid in which the particles, usually meaning solid but also definitely including liquid microparticles, are distributed.

Depending on the relationship of particle size to the wavelength of the light to which the scattered light area is exposed, different reflecting and scattering mechanisms take effect with different particles or types of particles. While it can be expected under certain conditions of particle size to incident light wavelength that scattered light will be observed in all spatial directions from a particle, other intensity distributions per reflecting and/or scattering particle result under other conditions of wavelength to particle size, for example solid angle-related or polarization-related intensity distributions.

In other words, the solid angle-related scattered light distribution of a particle onto which a light beam illuminating the particle falls is not only dependent on the wavelength of the incident light, but also as the case may be on the viewing angle, the particle size, the refractive index of the particle medium as well as the polarization of the incident radiation.

In the range of very small particles, in each case relating to the wavelength of the excitation light, an elastic scattering mechanism of the incident electromagnetic waves, known as Rayleigh scattering, generally predominates. In one range within which the wavelength of the energizing light corresponds approximately to the particle size, the scattering mechanism of the elastic scattering of the incident electromagnetic waves can be described by the Mie theory which, while describing an accurate solution to the scattering process, requires presupposition of the particle geometry (spherical particles). With further increasing particle size, the scattering can be described by conventional particle geometrical refraction.

In the realm of Rayleigh scattering and in the realm of Mie scattering, the scattering intensities of the radiation scattered at the particles are functions of, among other things, the solid angle, the particle size (particle radius), the polarization plane, the scattering angle and the complex refractive index of the suspension medium; i.e. in particular air.

The spatial distribution of the light scattered by a particle itself has intensity profiles which are dependent on the viewing direction. During the scattering process, particularly within the realm of Rayleigh scattering and Mie scattering, the interacting components of diffraction, refraction and reflection on the respective scattering particle all play a part in these intensity profiles. Due to this interacting scattering process, not only are the intensity profiles directionally dependent, but the scattering intensities then also vary in their respective polarization directions.

Also playing a role in the detection of scattered light is the fact that, for example with output-based scattered light detection, the aperture of the optical sensor employed is finite. It is hereby then also necessary to take the spatial detection angle into consideration.

The above indicated interaction between different components during the scattering process thus comprises the interaction of diffraction, refraction and reflection at the particle. Hereby, and due to the restrictions of an optical sensor with respect to the spatial detection angle and due to the dependency of, among other things, the particle radius, the wavelength of the incident light, the refractive index of the surrounding medium, the scattering angle and the polarizing angle, the intensity profiles of the scattered light scattered by different types of particles depend particularly on the positioning of the sensor relative to the scattered light area and any polarizing filter there may be in front of the sensor.

The circumstance of the compositions of the particles which develop for example upon a certain type of fire exhibiting a characteristic distribution is hereby capitalized on, whereby superpositioning the different scattering mechanisms or scattering characteristics respectively in the scattered light area likewise yields respective characteristic, position-dependent and polarization-dependent intensity distributions. In other words, the intensity of the scattered light measured at a specific location about the scattered light area in relation to the time over which the particles develop; i.e. during the course of a fire for example, exhibits a location-related and polarization-related characteristic pattern.

While there can still be collisions between characteristic patterns related to different particle types, and thus different types of fire, in the case of just one measuring point about the scattered light area with only one polarization, the probability of such pattern-related collisions drops as the measuring points and/or the detected polarization directions increase.

BRIEF DESCRIPTION OF THE DRAWINGS

The above and further advantages of the embodiments herein may be better understood by referring to the following description in conjunction with the accompanying drawings in which like reference numerals indicate identically or functionally similar elements, of which.

Figure 1:
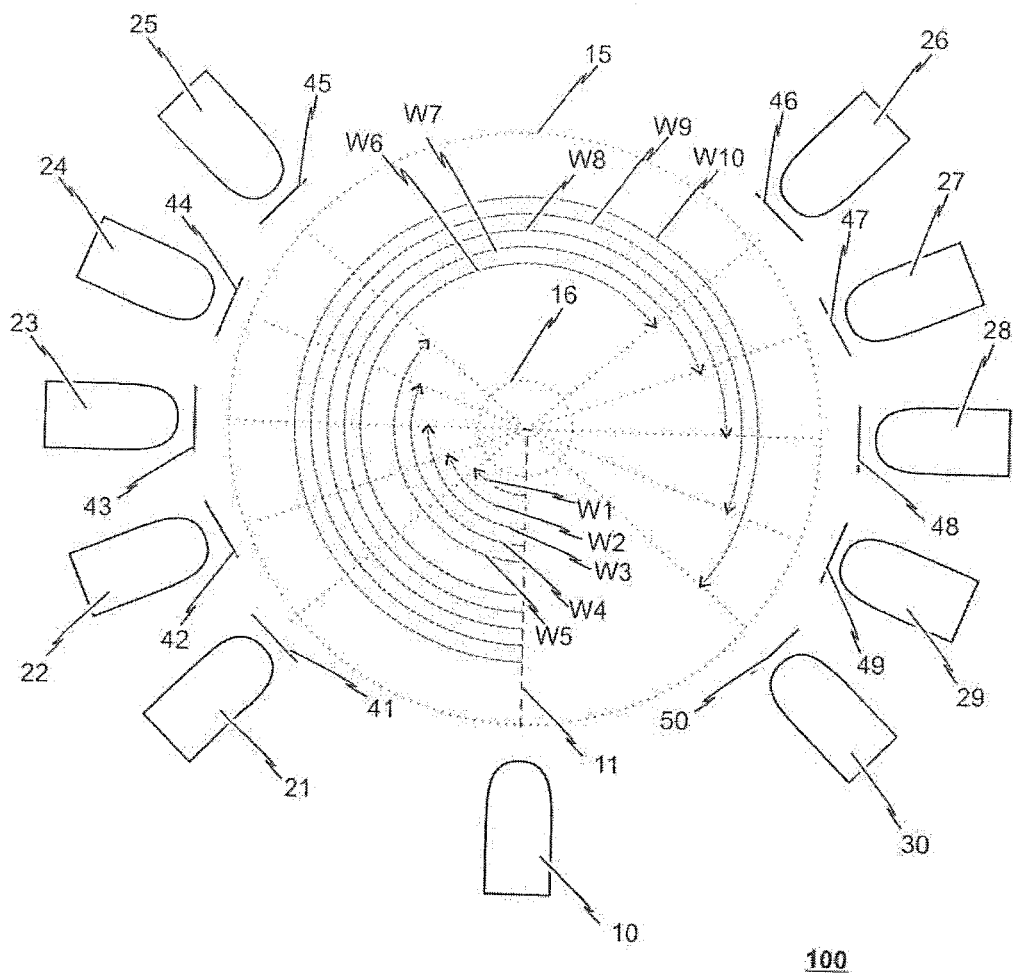
FIG. 1 is a schematic view of a device for detecting scattered light signals according to a first embodiment of the invention.

DETAILED DESCRIPTION OF AN
ILLUSTRATIVE EMBODIMENT

With regard to the inventive device for detecting scattered light signals, the objective is in particularly accomplished by the device comprising a light source, a plurality of optical sensors for detecting scattered light and an evaluation unit to evaluate the signals detected by the optical sensors. The light source hereby emits light in one scattered light area, whereby the incident light defines an incident axis. Each of the optical sensors is arranged at a sensor angle relative to the incident axis so as to detect scattered light from the scattered light area. At least one of the plurality of optical sensors, preferably an optical sensor arranged at a substantially right sensor angle, is configured as a reference sensor. To classify the type of any particle there may be in the scattered light area, the evaluation unit itself is configured to relate the signal profiles of the other optical sensors to the signal profile of the at least one reference sensor.

Of course it is also to be noted here that the light source emits a light beam at finite low expansion in the scattered light area; A preferential direction of the light source emission, i.e. in particular a light direction of largest relative intensity, is to be understood as the incident axis of the incident light, also in the case of an incident light beam of finite expansion.

It is hereby not imperative for the plurality of optical sensors to be configured discretely or even punctiform; flat or even cellular sensors such as, for example, charge-coupled devices (CCDs) or sensors produced with CMOS technology for detecting scattered light are just as conceivable, as long as they enable only one position-dependent evaluation of the incident light intensity. To be understood by a plurality of optical sensors is thus in particular also a cellular or flat device which enables position-dependent evaluation of the incident light intensity, for example in the form of cellular or planar coupled sensor points.

Any type of photosensitive semiconductor component such as e.g. photodiodes, but also photoresistors, phototransistors or photomultipliers, are particularly suitable as optical sensors (photodetectors).

It is likewise to be noted that each of the sensor angles of the plurality of optical sensors differ from one another. The optical sensors are thereby normally arranged in one plane so that the sensor angles, which are in each case relative to the incident axis of the excitation light, can be defined within the same plane. It is to be noted in conjunction hereto that the statements made previously with regard to the finite expansion of the light beam emitted by the light source naturally also apply to the detecting direction of the optical sensors, on the basis of which the respective sensor angle of an individual sensor is determined.

In a case in which individual instances of the optical sensors do not lie in a common plane, meaning in a case in which in particular the incident axis and individual sensor axes do not intersect (incident axis and sensor axes are skew lines), the sensor angle is to be understood as that angle which can be defined between those parallels to the incident axis and those parallels to the sensor angle which intersect at one point in space.

It is further to be noted that the relating of the other optical sensors' signal profiles to the signal profile of the reference sensor is expediently a normalization to the signal strength of the reference sensor. Hereby conceivable for example is a continuous normalization over time of the respectively measured signal profiles; i.e. with time-discrete signal sampling, for example, a normalizing of each individual sample of each of the other optical sensors' measuring signal to those samples of the reference sensor's signal profile which correspond to the same sampling instance.

Such a relating to the signal profile of the reference sensor, i.e. in particular such a normalizing to the signal of the reference sensor, is however also possible in the context of regression of the individual measuring points over the time elapsed, wherein the slope to the regression lines of the reference sensor is fixed at one in this case. For the remaining sensors, reference is made to the signal strengths of the reference sensor for performing the applicable regressions of the signal strengths of the sensors for the respective sensor, which in the ideal case are proportional to the measured scattered light intensity, such that the slopes to the best-fit line for the remaining sensors are in relation to the slope of the reference sensor normalized to one.

The inventive device for detecting scattered light signals has a series of advantages compared to the previously known devices. For instance, using a plurality of optical sensors at different detection angles yields an economical and energy-saving possibility of reliably and precisely classifying the type of particles present within the scattered light area. Particularly the providing of a plurality of optical sensors ensures the reliable allocating of particle patterns characteristic of certain types of particles. While pattern collisions are possible with individual scattered light sensors, particularly when noise-canceling or noise-reducing regression methods are used, whereby misclassifications can then result, the providing of a plurality of optical sensors greatly reduces the possibility of such pattern collisions. The detection and classification accuracy hereby increases without needing to use for example expensive and energetically uneconomical gas sensors or the like.

Because one of the plurality of optical sensors is used as the reference sensor; i.e. its detected signal profile being used as the reference signal, the individual signal profiles are largely independent of the absolute scattered light intensities, which decreases the calibration complexity and further simplifies the classification.

It is to be noted in conjunction hereto that with a continuous relating of the signal profiles to the signal profile of the reference sensor at each sampling instance, the signal profiles as a whole always have the reference sensor as a reference value; this enable a simple possible comparison with (likewise normalized) stored data for the purpose of classifying any particles which may be present in the scattered light area.

Classifying the particle type enables differentiating between a real fire and a false variable. In particular the level of reliability against false alarms can thus be significantly increased. For example, the smoke from a cigarette can hence be recognized as a disturbance variable and this can be forwarded as information. The smoke from a cable (smoldering fire), however, would accordingly trigger an alarm.

Correspondingly, according to one aspect of the present invention, it is further provided for the evaluation unit to be designed so as to distinguish between a fire parameter and a false variable, preferably automatically as a function of the classified particle type. In conjunction hereto, it is for example expedient to further provide for an alarming device allocated to the evaluation unit, same being designed to preferably automatically emit an alarm or an all-clear signal as a function of the classified particle type. It is hereby advantageous for the particle type(s) for which the alarming device will issue an alarm to be predefined or predefinable. It is hereby for example conceivable for a fire alarm to be signaled automatically upon the termination of the classification process, whereby this in particular ensues irrespective of any alarm thresholds; i.e. alarm threshold-independent.

The inventive classification of particle type not only increases the reliability against false alarms but also enables the initiating of targeted manual or automatic fire fighting measures as a function of the classified particle type. In conjunction hereto, it is particularly advantageous for a fire alarm to be signaled independently of any alarm thresholds when a steady pattern is reliably detected in the course of classification. Alternatively hereto, it is however also expedient for certain classifications to result in a fire alarm, while reference to a false variable is emitted when another type of particle is detected in the course of classification.

According to a further aspect of the inventive solution, it is provided for the evaluation unit to be further designed so as to compare the data obtained from the signal profiles of the signals detected from the plurality of optical sensors to signal patterns. Such a comparison preferably ensues continually over time. With a sufficiently high enough degree of correspondence between the signal profiles of the detected signals and one of the signal patterns, an identification signal identifying the classified particle type is then emitted.

It is to be noted in conjunction hereto that the term "pattern signal profiles" in the case of a plurality of optical sensors refers to an array of signal profiles; i.e. the signal profile over the time axis of each of the sensors employed is compared to the corresponding pattern signal profile of the respective sensor from the array of pattern signal profiles. Of course, the term "signal profile" or "pattern signal profile" is also in this case not to be in turn interpreted to the effect that only the actually recorded signal profiles of the individual sensors are to be compared to one another without for example performing a signal processing of the signals. Thus, it is also conceivable in this case, in which the evaluation unit is designed to independently compare the signal profiles to pattern signal profiles, to perform a regression of the signal profiles, for example after normalizing to the signal of the reference sensor and the respective slopes of the best-fit lines of the detected signals to the array of pattern signal profile slopes.

It is to be noted that for such a comparison to pattern signal profiles, the signal profiles are for example chronologically buffered in sections, with a suitable chronological comparison interval thereby being selected. It is for example expedient to select the comparison interval so as to achieve a detection accuracy which is sufficiently high enough for the classification while at the same time ensuring that a predefined (for example by external conditions, standards or other regulations) maximum temporal delay until the identification signal is output is not exceeded.

Of course a "concurrent" buffering, for example in a ring buffer, is also possible, whereby a respective likewise concurrent memory of said ring buffer corresponding to the comparison interval is then utilized for the comparison. A delay of this sort can then be extenuated in this case.

The pattern signal profiles are hereby preferably logged in test scenarios (test fires and the like) with a homogeneous or similar light source and plurality of optical sensors arrangement and stored in a suitable memory. It is to be noted hereby that such a logging of the pattern signal profiles is naturally performed with the same spatial arrangement of sensors (or possibly even more sensors) as will later be employed for the evaluation in the inventive device for detecting scattered light signals.

The degree of correspondence on which the comparison is based is either predefined or can be set by a user or operator. Degree of correspondences can hereby be determined based on conventional statistical or other suitable procedures, particularly conventional and known methods of pattern matching.

The identification signal can be a signal suited to further digital or analog processing which for example applicably encodes the detected particle type (i.e. the classified type of fire or the classified type of other particles). In the simplest case, however, it is also possible for the identification signal to be output to a suitable optical display, for example a display screen or the like, on which a user or operator can then read the classification. It is also possible for the identification signal to activate an electronic or electromechanical switch such as for example a relay or the like so as to communicate the presence of a fire, for example to an additionally connected mechanism.

By the largely automated comparing of the detected signals to pattern signal profiles (or an array of pattern signal profiles respectively), it thus becomes simple to target further fire type-dependent actions for selection (selecting a suitable fire extinguishing agent or inertization means, selecting a suitable inerting level, etc) so as to be able to take effective action against a fire. While it is not imperative for such a comparison of detected signals to pattern signal profiles to run automatically, such an automated and largely autonomous classification of fire type has the advantage of an automated, fire type-dependent further processing of the signal as well as saving considerable time for any potential operator or user.

With respect to the design of the evaluation unit, it is on the one hand preferably provided for same to be capable of determining a particle level as a function of the intensity of the scattered light detected by the reference sensor. On the other hand, it can be of additional advantage for the evaluation unit not to perform pattern matching until the particle level exceeds a lower threshold value ("minimum particle level"). Both further developments of the inventive detection device serve to further improve the detection accuracy, which is accompanied by further reducing false detections.

According to a further aspect of the invention, it is provided for the light source to emit substantially monochromatic light in the wavelength range of approximately 560 to 420 nanometers. The light source preferably emits light in the range of between approximately 470 to approximately 450 nanometers. These wavelengths correspond to a spectrum of green to blue light. The use of relatively short-wavelength light hereby has the advantage that the prevailing particle sizes usually present in typical fires predominantly exhibit Rayleigh and Mie scattering in which short-wavelength light is scattered substantially more strongly than relatively long-wavelength light, thereby resulting in an advantageous distribution of intensity at the optical sensors detecting the scattered light.

According to a further aspect of the invention, it is provided for at least one of the optical sensors to comprise a polarizing filter for polarizing the scattered light to be detected.

Using a polarizing filter on at least one of the optical sensors can further decrease the risk of pattern collisions by the additional evaluation of this additional scattering characteristic, which improves the detection accuracy.

It can be provided in conjunction hereto for a plurality of the optical sensors and preferably each of the optical sensors to comprise a polarizing filter. The polarization planes of at least two polarizing filters are hereby arranged substantially perpendicular to each other. Rotating the polarization plane of at least one polarizing filter relative at least one further polarizing filter, whereby these polarizing filters are allocated to different optical sensors from the plurality of sensors, will then ensure that sufficiently differing signal profiles or pattern signal profiles respectively will still result, even when the distribution of intensity for a specific type of particle depends only minimally on the viewing direction, but in return all the more on the polarization direction, which even in this case further reduces the risk of pattern collisions and again increases the detection/classification accuracy. The increase in accuracy attainable by using the polarizing filters as well as their specific alignment to one another can hereby be achieved extremely economically since polarizing filters are easy and cheap to manufacture.

According to a further aspect of the invention, it is provided for each of the optical sensors to be substantially aligned toward a common scattered light area detection region.

Such an aligning to a common detection region, which is a subset of the scattered light area and usually surrounds a common scattered light center, can again further improve the detection accuracy. In particular hereby taken into account is the fact that the aperture of the optical sensors is normally finitely small and thus yields a form and/or expansion of the reception lobe of the respective optical sensor in dependence on the solid angle. Aligning to a common detection region can thus further reduce measuring inaccuracies.

According to a further aspect of the invention, it is provided for individual or all the optical sensors to be designed as photodiodes. The pn junction is directly exposed to the scattered light to be detected in such semiconductor diodes, wherein the photons of the scattered light in the pn junction cause an electron-hole pair to form. Such photodiodes are relatively cheap and allow simple circuitry structuring, whereby no complex electronic control is necessary. Depending on the mode of operation (type of characteristic), such a photodiode can additionally be operated through multiple orders of magnitude, preferably in the linear range.

However, using other suitable optical sensors such as for example phototransistors or even photomultipliers is of course also possible. Photomultipliers have orders of magnitude higher sensitivity than photodiodes and are based on the effect of secondary electron multiplication. Utilizing the external photoeffect (releasing electrons from an electrode layer by incident photons) accelerates these released primary electrons by means of an acceleration voltage to further, downstream electrodes at which a further release of secondary electrons, now induced by the respectively accelerated electrons, occurs. The quantity of the incident multiplied electrons on an anode are ultimately evaluated and converted into a further processable electrical signal.

In conjunction hereto, or even separately, it is also conceivable for the light source to be a light-emitting diode. Such a light-emitting diode to excite the scattered light area is very economical and also available in the advantageous wavelength ranges. For a conceivably necessary temperature compensation of the inventive device for detecting scattered light signals it is for example conceivable to very easily operate such a light-emitting diode in pulsed mode so as to reduce the development of heat. Of course, continuous excitation is however also possible—given acceptance of greater heat development if applicable.

According to a further aspect of the invention, it is provided for the device to comprise one optical sensor at a first sensor angle, one optical sensor at a second sensor angle and one optical sensor at a third sensor angle, wherein the first sensor angle is an acute angle and totals 360° together with the second sensor angle, and wherein the third sensor angle is an obtuse angle.

This particular disposition enables individual particle type patterns to be obtained which are very easily distinguishable from one another with relatively few sensors in a specific spatial arrangement. Preferably, the first sensor angle hereby amounts to approximately 45°, whereby a preferable magnitude of approximately 315° results for the second sensor angle. The third sensor angle preferably amounts to approximately 112°. The reference sensor is preferably arranged at a sensor angle of approximately 90°. A reference sensor arranged at a right angle has hereby proven to be particularly advantageous in normalizing the signals of the respective other optical sensors given a plurality of conceivable particle types (particle properties).

In other words: With the reference sensor arranged at a right angle, the risk of pattern collisions can be reduced compared to other reference sensor angles. Moreover, higher classification accuracy can be achieved with the reference sensor arranged at a right angle than at other reference sensor angles, and same achieved relatively independently of the total number of further sensors provided in the respective configuration and also relatively independently of their sensor angles.

When an economical construction with only a few sensors is provided, the type of fire can then be more precisely classified by the providing of a reference sensor arranged at a right angle compared to other reference sensor angles.

A reference sensor arranged at a right angle is advantageous particularly also with respect to the quality of the detected signals, since a reference sensor which is arranged at a 90° angle exhibits a "neutral" angular position such that it is neither a forward emitter nor a reverse emitter. Tests have shown that the 90° angle for the reference sensor yields the best pattern for substance differentiation.

According to a further aspect of the invention, it is provided in the just described specific arrangement of the first, second and third sensor as well as the reference sensor for the optical sensor at the first sensor angle, the optical sensor at the second sensor angle and the optical sensor at the third sensor angle as well as the reference sensor to each comprise a polarizing filter. The polarizing filters of the reference sensor, the optical sensor at the first sensor angle and the optical sensor at the third sensor angle are hereby aligned with one another in a first polarization plane, whereas the polarizing filter of the optical sensor at the second sensor angle is aligned in a second polarization plane perpendicular to the first polarization plane. Such an arrangement of the individual polarization planes of the polarizing filters has proven particularly advantageous as far as the special characteristics of the individual determined patterns becoming even clearer, thereby again further improving the detection/classification accuracy.

According to a further aspect of the invention, it is provided for the evaluation unit to be designed to determine the degree of correspondence by correlating the data obtained from the distribution of the signal profiles of the detected signals according to a principal component analysis into clusters (BUC, BAU, PUR, HEP, ABS, PAP, PAE, PVC, ZIG, ZRE, MEH, ZEM, TEP) of the signal patterns. Such a correlation; i.e. applying a known stochastic method to the detected signals or to the pattern signals respectively, allows the similarity of the detected signal profiles to the pattern signal profiles to be easily and effectively determined, whereby the computational expenditure and thus the circuitry complexity can be kept within reasonable limits, thereby being economical.

It is however also equally possible for the evaluation unit to be designed to determine the degree of correspondence by distance determination of the data obtained from the distribution of the signal profiles of the detected signals according to a principal component analysis into clusters (BUC, BAU, PUR, HEP, ABS, PAP, PAE, PVC, ZIG, ZRE, MEH, ZEM, TEP) of the signal patterns.

Such a principal component analysis (PCA) hereby has the advantage of using a non-parametric method to extract relevant information on the dataset of the noisy scattered light signals, whereby in principle no knowledge is needed of the mathematical degrees of freedom of the underlying scattered light distribution. It is hereby taken into account that by determining the pattern signal profiles, more dimensions than are actually needed are recorded, whereby the principal component analysis serves, without a parametric method being necessary, to reduce the dimensions needed for the evaluation so as to be able to readily extract the relevant information (principal components).

It is however also equally possible for the evaluation unit to be designed to determine the degree of correspondence by neuronal network evaluation of the data obtained from the distribution of the signal profiles of the detected signals according to a principal component analysis into clusters (BUC, BAU, PUR, HEP, ABS, PAP, PAE, PVC, ZIG, ZRE, MEH, ZEM, TEP) of the signal patterns. Said neuronal network preferably has at least 38 neurons. Neuronal network evaluation enables a simple "training" of the inventive device with pattern signal profiles at concurrently high detection accuracy during the evaluation of signals detected from signal profiles.

According to a further aspect of the invention, it is provided for the signal patterns to correspond to particle distribution signals of one or more particle emissions from among the group of dust emission, vapor emission, tobacco smoke emission, smoldering paper fire, smoldering cardboard fire, open paper fire, open cardboard fire, ABS fire, n-heptane fire, PVC fire, cotton fire, wood fire or other particle emission occurrences.

It is hereby possible to be able to output extinguishing instructions or even automatic extinguishing or inerting actions as a function of a specific group of typically occurring fires. When other particle emissions which cannot be assigned to any of the specific occurrences are detected, a "worst case scenario" can then in this case be assumed and in each case a full inerting or fire-fighting response with all available means for example initiated. In all other cases, selective fire-fighting is possible given knowledge of the specific type of fire.

According to a further aspect of the invention, it is provided for the device to be used in an aspirative fire detection system. The aspirative fire detection system comprises a preferably controllable active air supply for feeding air to be classified into the scattered light area of the device for detecting scattered light signals. Use in such an aspirative fire detection system is then above all advantageous or may at certain times even be prescribed, if for example an enclosed room is kept at a constant base inertization level. In this case, it is possible that the particles will not reach the scattered light area when a fire occurs without an aspirative fire detection system. An active air supply into the scattered light area can thereby improve the detection accuracy, particularly in enclosed rooms at base or permanent inertization levels.

Particularly in this context it is further conceivable for the device to comprise a mechanism for detecting a minimum particle level as well as a mechanism for selectively permitting the feed of air to be classified into the scattered light area.

The supplying of the air to be classified is then precisely enabled when an exceeding of the minimum particle level is detected. This thereby ensures that no air flows through the scattered light area of the inventive device when idle so as to protect the optical sensors from impurities. Not until a minimum smoke level (minimum particle level) occurs is the air feed then enabled into the scattered light area.

It is to be noted at this point that the lowering; i.e. the reducing of the oxygen content, can be realized for example by introducing a suitable inert gas such as for example nitrogen, which is preferably generated by means of a nitrogen generator. The term "controlled reduction" equally refers to a technically controlled as well as a preferably regulated process. In one applicable technically regulated process, which preferably runs automatically, the oxygen concentration in the enclosed room to be rendered inert is for example continuously measured by a suitable sensor and continuously compared to an ideal or default value which is to be achieved as the target value by appropriately introducing inert gas. Said target value is preferably set automatically by an inerting system comprising an inventive device for detecting scattered light signals, meaning as a function of a fire type classified by means of the device, a suitable or sufficient inertization level is determined to effectively extinguish the specific burning material according to need.

To be mentioned in conjunction hereto is that the inertization level; i.e. the target oxygen concentration, is usually maintained over a certain time period, wherein a technical regulating system lends itself in turn hereto. It can, for example, implement an extinguishing action by inertization, which requires a certain amount of time to conclude.

Of course it is also possible that after the device classifies a fire, such a target value is determined manually using a table and manually entered into an applicable inerting system.

According to a further aspect of the invention, it is provided for the control signal to be the identification signal which identifies a recognized pattern signal profile and that the inerting system be further designed to automatically set the reduced oxygen content.

With regard to the inventive method, the objective is accomplished particularly by a method for detecting scattered light signals which comprises the method steps of supplying light, detecting scattered light, and the preferably continuous relating of optical sensor signal profiles to a signal profile of a reference sensor. In the method step of supplying light, the light is preferably supplied at a wavelength range of from approximately 560 to approximately 420 nm, particularly preferably from approximately 470 to 450 nm, and particularly from a light-emitting diode in a scattered light area. The incident light hereby defines an incident axis. In the method step of detecting scattered light, scattered light which reflects on any particles which may be present in the scattered light area is detected by means of a plurality of optical sensors, wherein the plurality of optical sensors is preferably a plurality of photodiodes each arranged at a sensor angle relative to the incident axis. With regard to the method step of the preferably continuous relating of optical sensor signal profiles to a signal profile of a reference sensor, the signal profiles for classifying the type of particle which may be present in the scattered light area are related to the optical sensor signal profiles on the reference sensor signal profile, preferably to the signal profile of a reference sensor arranged substantially at a right sensor angle.

The advantages described earlier with respect to the inventive device also apply analogously to the inventive method.

According to a further aspect of the invention, it is provided with respect to the method for the method to further comprise the method step of preferably continuously comparing the data obtained from signals detected from the signal profiles with the signal profile of the reference sensor to signal patterns and the method step of emitting an identification signal upon a sufficiently high enough degree of correspondence to one of said signal patterns, preferably to an inertization system for the controlled reduction of the oxygen content in an enclosed room, wherein the identification signal identifies the type of particle as classified.

DESCRIPTION

FIG. 1 shows a schematic view of a first embodiment of an inventive device 100 for detecting scattered light signals. The device 100 comprises a light source 10, which emits light along an incident axis 11 in a scattered light area 15 indicated by dotted lines.

The light source 10 is designed as a light-emitting diode in the embodiment of FIG. 1 and thus emits light at a finitely small lobe. The incident axis 11 is expediently defined such that it runs along the lines which would connect the respective centers of the radiation cone upon the light source light cone being depicted onto the sectional planes extending into the scattered light area 15 perpendicular to the paper plane of FIG. 1. The light source 10 emits substantially monochromatic light in the wavelength range from approximately 560 to approximately 420 nm (green to blue range of visible light). The light source 10 preferably emits light in the range from approximately 470 to approximately 450 nm (blue range of visible light).

Light at this wavelength range is more strongly scattered by the scattering mechanisms governing the particles (Rayleigh/Mie scattering) than longer wavelength light, which leads to relatively high signal levels at the scattered light detectors 21, 22, 23, 24, 25, 26, 27, 28, 29, 30 compared to longer wavelength light and thus results in a relatively good signal-to-noise ratio.

In the first embodiment according to FIG. 1, a plurality of optical sensors 21, 22, 23, 24, 25, 26, 27, 28, 29, 30 is arranged in the same plane in which the light source 10 is also arranged, each sensor being arranged at an associated sensor angle W1, W2, W3, W4, W5, W6, W7, W8, W9, W10 (mathematically negative assumed in FIG. 1) related to the incident axis 11 and aligned in the direction of a detection region 16 surrounding the center of the scattered light area 15.

The sensor angles W1, W2, W3, W4, W5, W6, W7, W8, W9, W10 of optical sensors 21, 22, 23, 24, 25, 26, 27, 28, 29, 30 are thus in each case different from one another according to the first embodiment. Furthermore, the optical sensors 21, 22, 23, 24, 25, 26, 27, 28, 29, 30 are arranged in one plane; i.e. the plane of the paper according to the FIG. 1 depiction. The sensor angles, which are in each case relative to the incident axis 11 of the excitation light, can thereby be defined within the same plane. In conjunction hereto, it is to be considered that the previous remarks made above related to the finite expansion of the beam emitted by the light source 11 naturally also apply to the detecting direction of the optical sensors 21, 22, 23, 24, 25, 26, 27, 28, 29, 30, on the basis of which the respective sensor angle W1, W2, W3, W4, W5, W6, W7, W8, W9, W10 of an individual sensor 21, 22, 23, 24, 25, 26, 27, 28, 29, 30 is determined.

Deviating from this, it is also possible for individual optical sensors 21, 22, 23, 24, 25, 26, 27, 28, 29, 30 to not be arranged in a common plane. In other words, in a case in which particularly the incident axis 11 and individual sensor axes of the sensors 21, 22, 23, 24, 25, 26, 27, 28, 29, 30 do not intersect (incident axis 11 and sensor axes being skew lines), the sensor angle W1, W2, W3, W4, W5, W6, W7, W8, W9, W10 is to be understood as that angle which can be defined between that parallel to the incident axis 11 and that parallel to the sensor axis intersecting at one point in space.

In the first embodiment according to FIG. 1, each of the optical sensors 21, 22, 23, 24, 25, 26, 27, 28, 29, 30, which in the embodiment according to FIG. 1 are designed as photodiodes, is provided with a respective polarizing filter 41, 42, 43, 44, 45, 46, 47, 48, 49, 50. Each of the polarizing filters 41, 42, 43, 44, 45, 46, 47, 48, 49, 50 polarizes any scattered light there may be striking the optical sensors 21, 22, 23, 24, 25, 26, 27, 28, 29, 30, which is scattered by any particles to be classified there may be within the scattered light area 15 when the excitation light from the light source 10 strikes the particles.

Instead of photodiodes, any other type of photosensitive semiconductor components are in principle also conceivable as optical sensors 21, 22, 23, 24, 25, 26, 27, 28, 29, 30 (photo-detectors) such as, for example, photoresistors, phototransistors or photomultipliers.

Polarizing filters 41, 42, 43, 44, 45 of optical sensors 21, 22, 23, 24, 25 are hereby aligned in a common polarization plane while polarizing filters 46, 47, 48, 49, 50 of optical sensors 26, 27, 28, 29, 30 are aligned perpendicular to said common polarization plane.

It is to be noted at this point that particularly with flat or cellular sensors as discussed above, such polarizing filters can also be deposited directly on the sensor chip; i.e. on the sensor chip surface. In other words, particularly with integrated flat or cellular sensor solutions (CDD, CMOS or the like), a layer can be provided on the sensor surface, respectively the sensor array, at the individual sensor locations, or detecting locations respectively, which is in direct or indirect contact with the sensor chip and has a polarizing effect.

The optical sensor 23 which, according to the embodiment of FIG. 1, is arranged at a largely right sensor angle W3, serves as the reference sensor in this first embodiment; i.e. the detection signals of the other optical sensors 21, 22, 24, 25, 26, 27, 28, 29, 30 are related to the reference sensor 23 or its signal profile respectively.

It is to be further noted that the relating of the signal profiles of the other optical sensors 21, 22, 24, 25, 26, 27, 28, 29, 30 to the signal profile of the reference sensor 23 is expediently a normalizing to the signal strength of the reference sensor 23. Conceivable hereby is for example a continuous normalizing of the respectively measured signal profiles over time; i.e. in the case of time-discrete signal sampling, for example, a normalizing of each individual sample of each measuring signal of the other optical sensors 21, 22, 24, 25, 26, 27, 28, 29, 30 to that sample of the reference sensor 23 signal profile which corresponds to the same sampling instance.

Because of the relatively large number of optical sensors 21, 22, 23, 24, 25, 26, 27, 28, 29, 30 according to the first embodiment depicted in FIG. 1, pattern collisions and thus detection collisions can be largely prevented, meaning given a relatively large number of optical sensors as in the first embodiment according to FIG. 1, signal patterns and/or signal pattern arrays of high accuracy can be achieved. It is however pointed out that—depending on the respective application—quite considerably fewer optical sensors 21, 22, 23, 24, 25, 26, 27, 28, 29, 30 can be used and yet high detection accuracy can still be ensured, as will be described in greater detail below with reference to FIG. 2.

The intensity of the scattered light measured at a specific location around the scattered light area 15 exhibits—for example during a fire—a location-related and polarization-related characteristic pattern which can be reliably and easily detected with the device according to FIG. 1.

With conventional devices which only detect one single measuring location around the scattered light area 15 without a prefixed polarizing filter, it is highly probable that collisions will by all means occur between detection patterns of different types of fire. With the device according to the invention described in the first embodiment based on FIG. 1 having a plurality of optical sensors 21, 22, 23, 24, 25, 26, 27, 28, 29, 30, wherein one sensor 23 is a reference sensor, the probability of such pattern-related collisions decreases.

Figure 2:
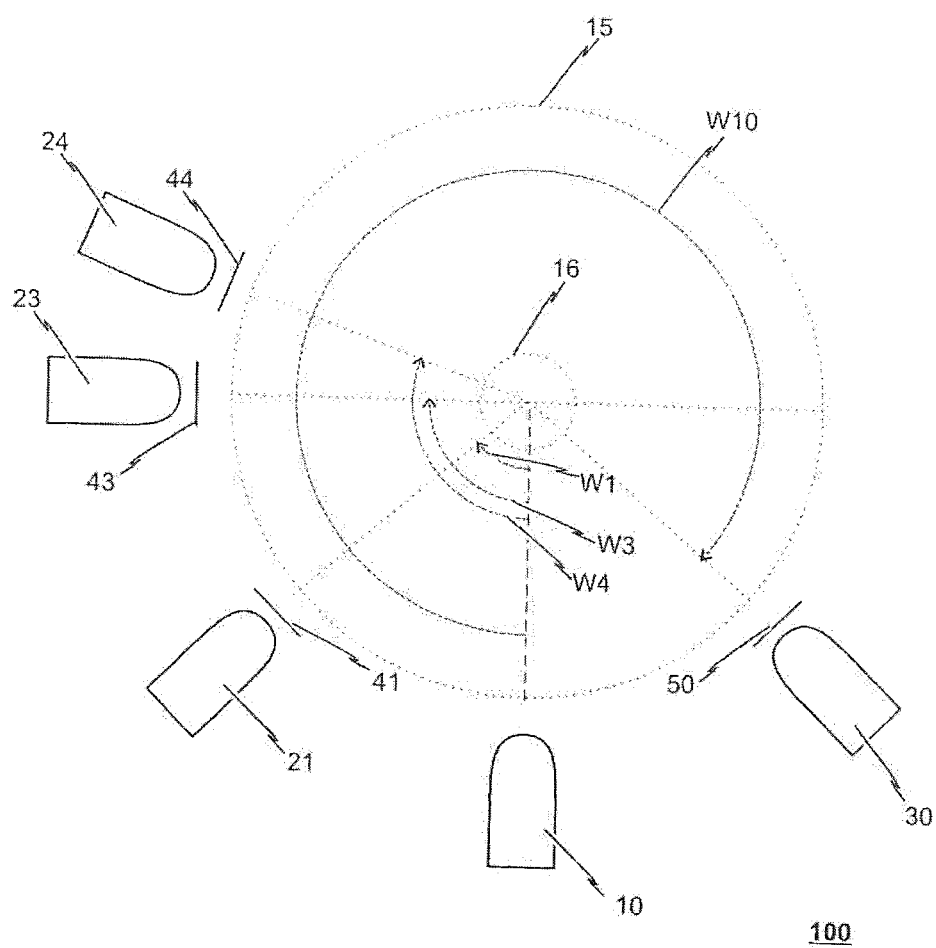
FIG. 2 is a schematic view of a device for detecting scattered light signals according to a second embodiment of the invention.

FIG. 2 shows the schematic structure of a second embodiment of the inventive device 100 similar to that as in FIG. 1, however with a clearly reduced number of optical sensors.

With respect to the configuration and the effect of the optical sensors 21, 22, 23, 24, 25, 26, 27, 28, 29, 30 and the light source 10 employed, the remarks made in connection with the first embodiment apply to the second embodiment.

In the device 100 for detecting scattered light signals, in addition to the light source 10, which is again designed as a light-emitting diode, only four optical sensors 21, 23, 24, 30 are provided which are arranged at respective sensor angles such as W1, W3, W4, W10 about the scattered light center 15. The optical sensor 23 arranged substantially at right sensor angle W3 serves again as the reference sensor. Also in the second embodiment, all of the optical sensors 21, 23, 24, 30 are provided with correspondingly arranged polarizing filters 41, 43, 44, 50.

Optical sensor 21 is hereby preferably arranged at an acute angle W1 of approximately 45°; sensor 30 arranged opposite thereto relative to light source 10 is preferably at an angle W10 of approximately 315° such that acute angle W1 and angle W10 equal a round angle; i.e. 360°. Optical sensor 24 is arranged at an obtuse angle W4, whereby the obtuse angle W4 preferably amounts to approximately 112°. While the polarizing filters 41, 43, 44 of optical sensors 21, 23, 24 are aligned in the same polarization plane, the polarization plane of polarizing filter 50 of optical sensor 30 is in contrast rotated by 90°. With the specific implementation according to the second embodiment of FIG. 2, despite a reduced number of sensors, significant characteristic signal patterns or signal pattern arrays can be determined, respectively scattered light signals detected at high detection/classification accuracy, with automatic classification by pattern matching to one of the signal pattern arrays as applicable.

Not shown in either FIG. 1 or 2 is an evaluation unit for evaluating the signals detected by the optical sensors 21, 22, 23, 24, 25, 26, 27, 28, 29, 30, which, with reference to the representations in the following figures, realizes the depicted normalizing of the signal profiles of the sensors to the signal profile of a reference sensor (reference sensor 23 in the embodiments according to FIGS. 1 and 2).

Expediently, such an evaluation unit is a digital evaluation unit, particularly a micro-computer, an embedded system or the like. In this case, sufficient amplitude resolution is ensured during a sampling of the optical sensors' signal values by the selecting of a suitable analog/digital converter. Sampling is furthermore obviously realized at a sufficiently high enough sampling rate to prevent aliasing errors.

Such an evaluation unit (not shown in FIGS. 1 and 2) is preferably configured to compare the detected signals of optical sensors (21, 22, 23, 24, 25, 26, 27, 28, 29, 30) to the signal patterns depicted in the following figures, preferably continuously. At a sufficiently high enough degree of correspondence to one of the signal patterns, such a correspondingly designed evaluation unit can preferably output an identification signal which identifies the particle type as classified.

Such an identification signal can preferably be output to a likewise not shown simple optical display (light-emitting diode or optical display screen or the like) or to a relay control. It is further possible for the identification signal to be output to an inertization system (likewise not shown in FIGS. 1 and 2), which implements a suitable inertization procedure for the specific type of fire based on the automatically classified fire type encoded in the identification signal.

Figure 3:
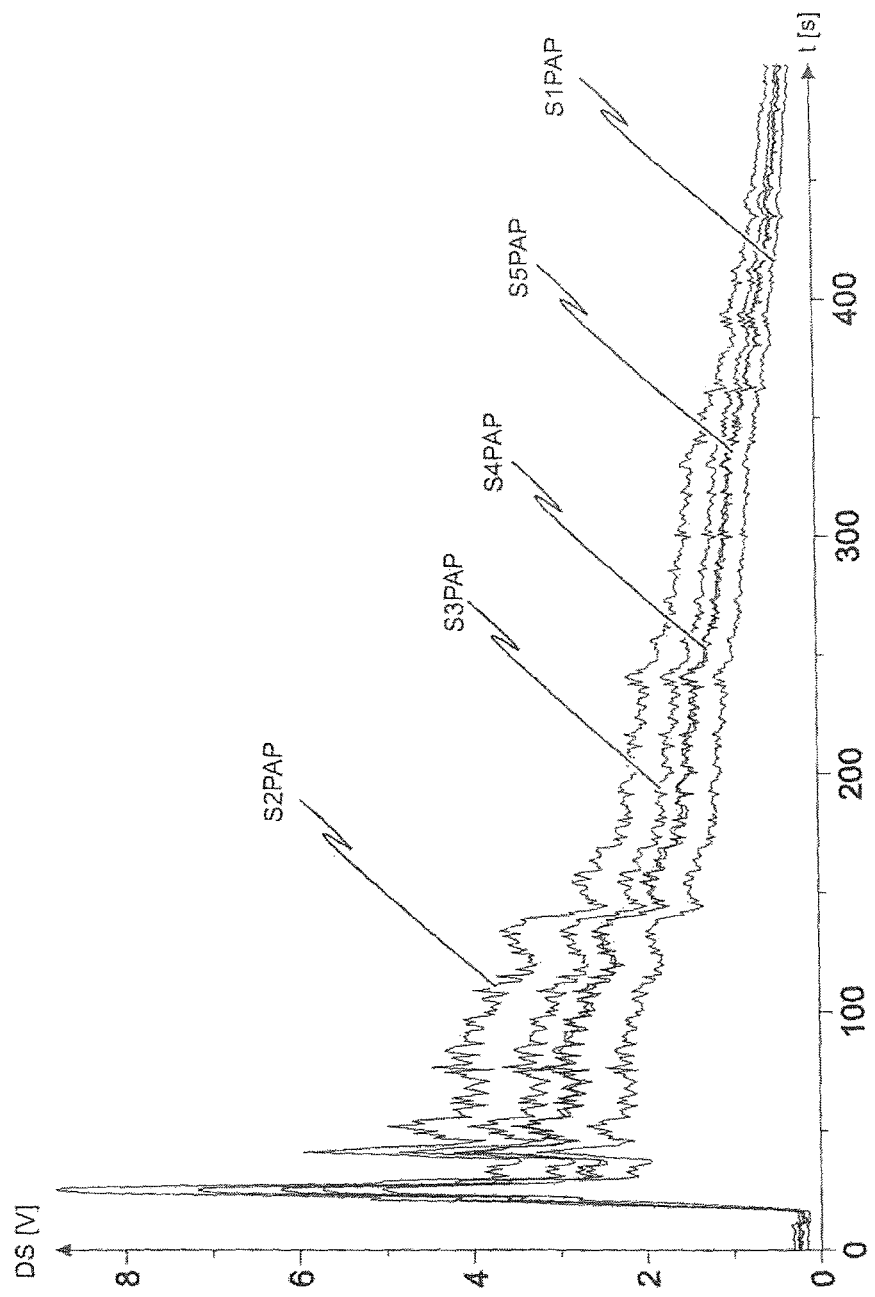
FIG. 3 is are signal profiles of the optical sensors employed in the device according to FIG. 1 on the figure's left side during a scattered light detecting procedure over time.

FIG. 3 shows a signal profile diagram of the optical sensors 21, 22, 23, 24, 25 from the first embodiment according to FIG. 1 during a first test measurement over the time axis. Depicted here are the output voltages and/or detection voltages DS of the optical sensors 21, 22, 23, 24, 25. The first test measurement depicted in FIG. 3 is realized with the device according to the first embodiment during an open paper fire so as to obtain characteristic pattern signal profiles of the optical sensors 21, 22, 23, 24, 25 arranged to the left of the incident axis in FIG. 1. Optical sensor 21 is hereby attributed to the signal profile identified as S1 PAP; the signal profiles S2 PAP, S3 PAP, S4 PAP and S5 PAP analogously correspond to the measurement signals emitted by optical sensors 22, 23, 24, 25 over a period of 0 to approximately 500 seconds. It is to be pointed out here that by selecting a sufficiently high enough sampling rate, time-discrete signal profile measurements can of course also be performed so that the signal profiles can be readily processed further in a digital processing system.

Figure 4:
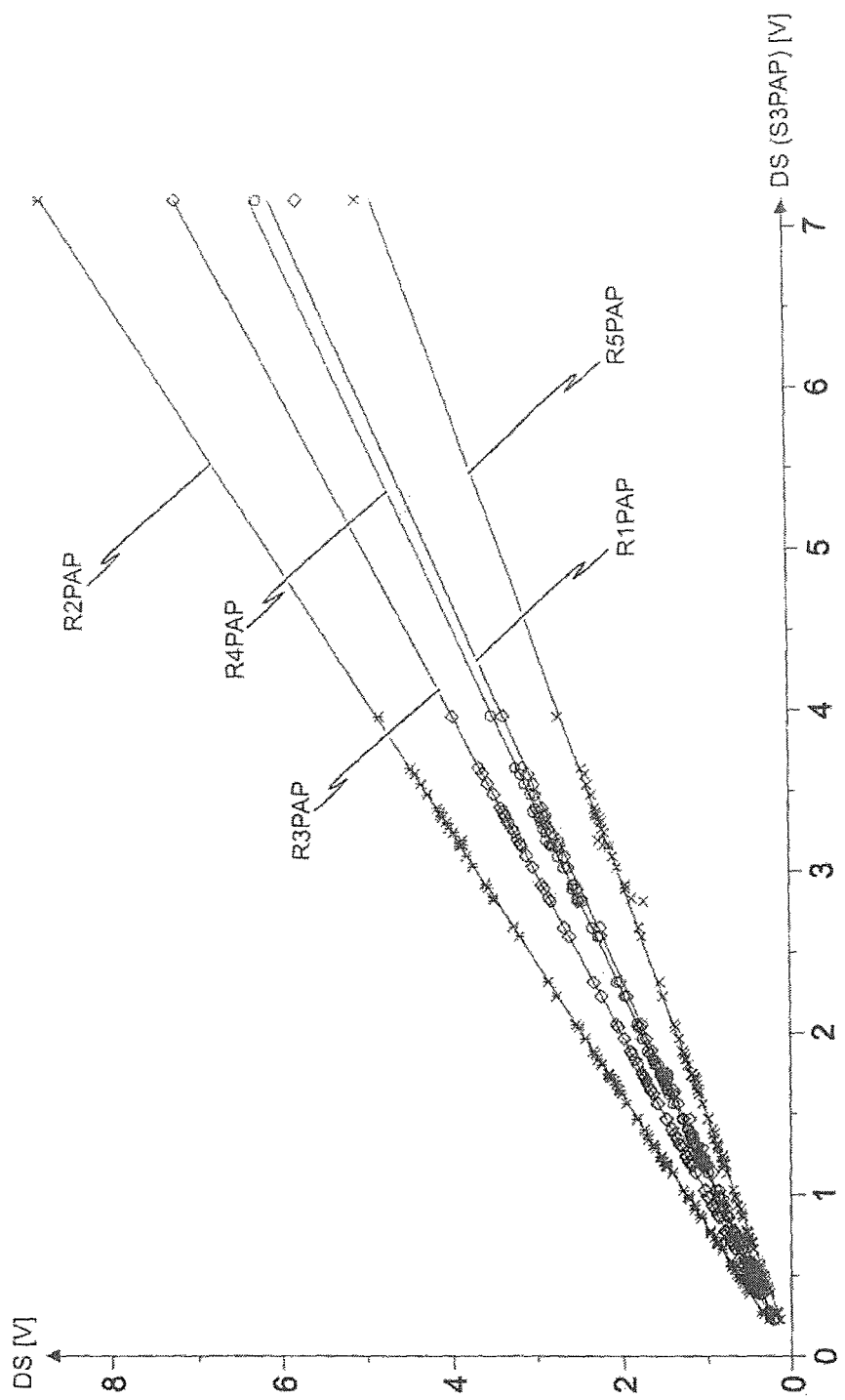
FIG. 4 is a depiction of regression lines of the signal profiles from FIG. 3 related to the signal of a reference sensor.

FIG. 4 depicts the regression lines associated with FIG. 3 following the relating of the individual measuring points from FIG. 3 to the output signal S3 PAP of reference sensor 23. After the thereby realized normalizing of the measurement signals to the output signal of reference sensor 23, the slope of its best-fit line R3 PAP amounts to one, whereas the slopes of the other best-fit lines R1 PAP, R2 PAP, R4 PAP and R5 PAP, relating to the optical sensors 21, 22, 24 and 25, differ from one.

Figure 5:
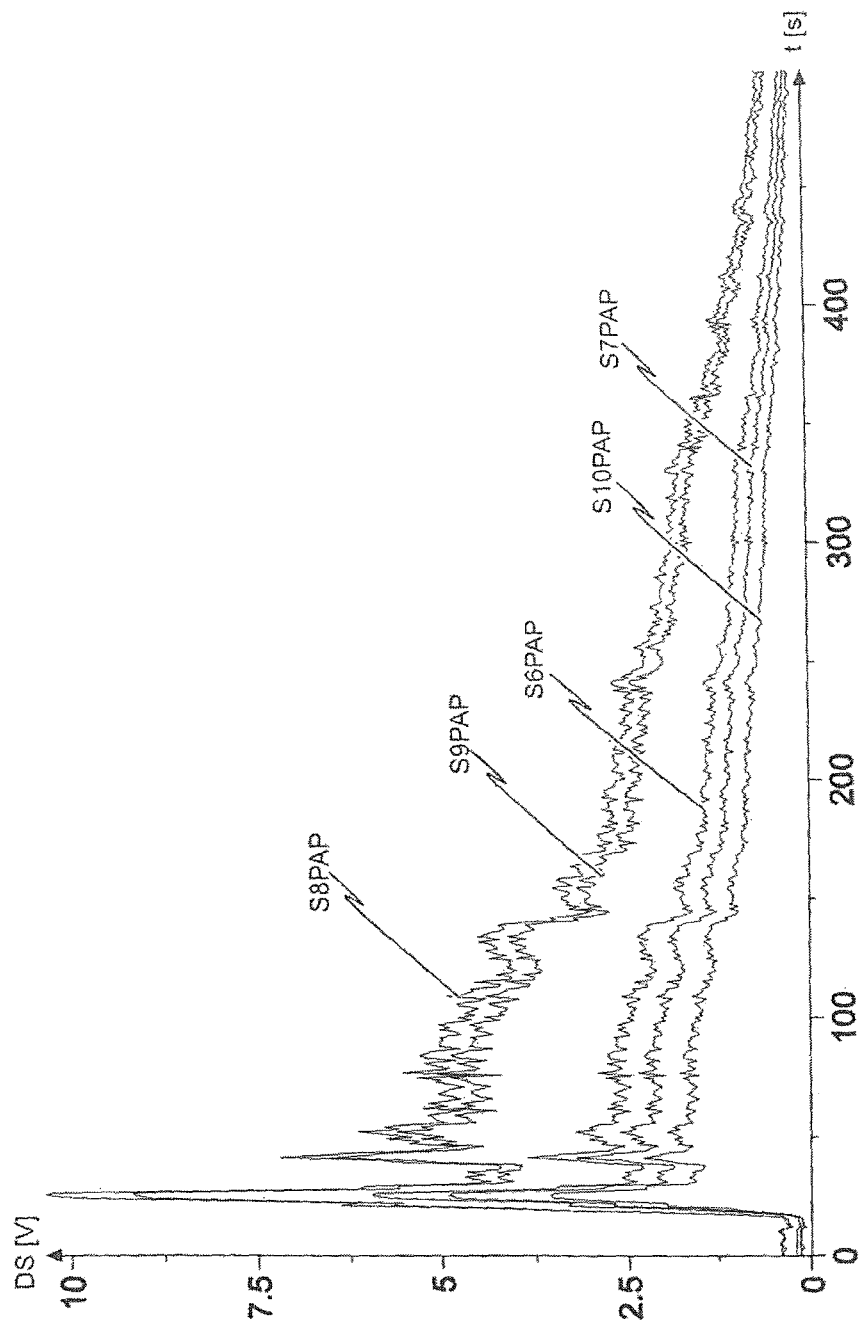
FIG. 5 are signal profiles similar to FIG. 3 for the optical sensors arranged on the right in FIG. 1.

FIG. 5 shows the signal profiles of the optical sensors 26, 27, 28, 29, 30 to the right of the incident axis in FIG. 1, likewise during a first test measurement during the above-cited open paper fire. The signal profiles S6 PAP, S7 PAP, S8 PAP, S9 PAP and S10 PAP hereby correspond to the signal profiles emitted by the optical sensors 26, 27, 28, 29, 30.

Figure 6:
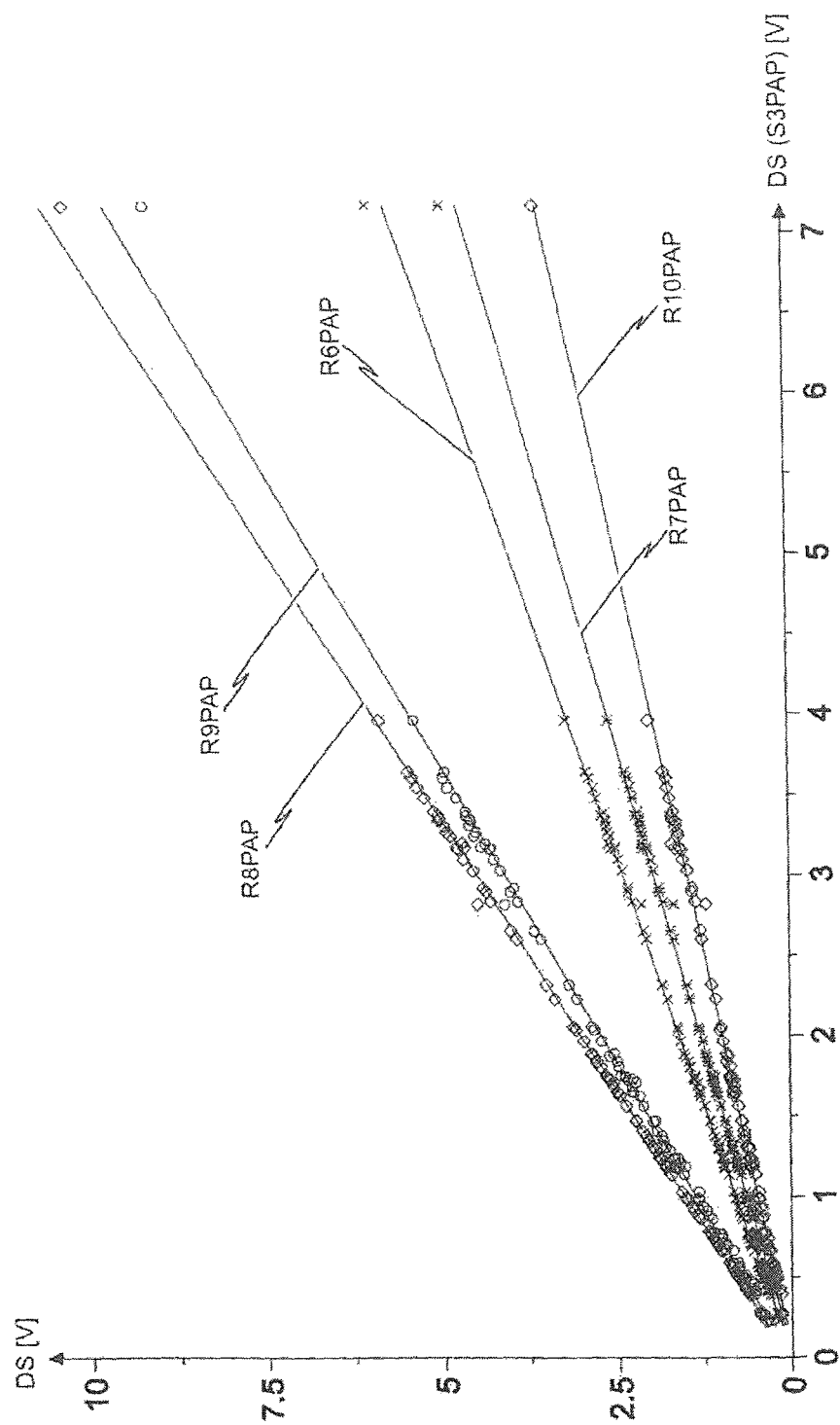
FIG. 6 are regression lines related to the same reference sensor analogous to FIG. 4 for the optical sensors arranged on the right in FIG. 1.

FIG. 6 in turn depicts the associated regression lines R6 PAP, R7 PAP, R8 PAP, R9 PAP and R10 PAP which again—analogously to the FIG. 4 depiction—are related to the detection signal profile of reference sensor 23 (i.e. signal profile S3 PAP).

Figure 7:
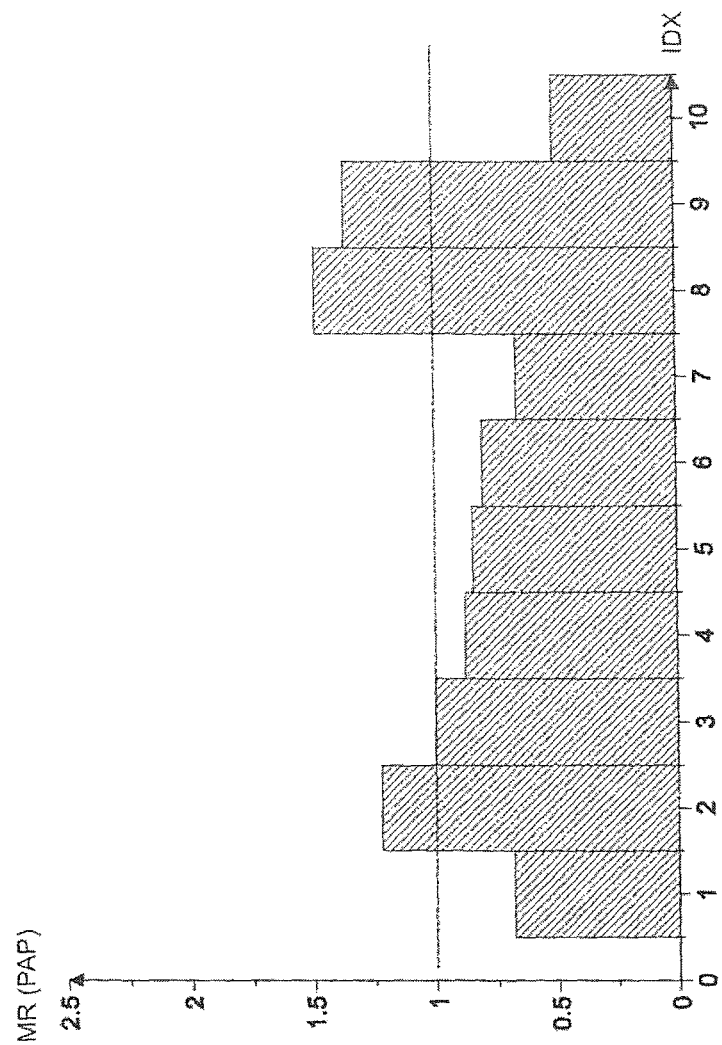
FIG. 7 are the slopes of the best-fit lines determined in FIG. 4 and FIG. 6 related to the sensor index for the particle measurement performed.
Figure 8:
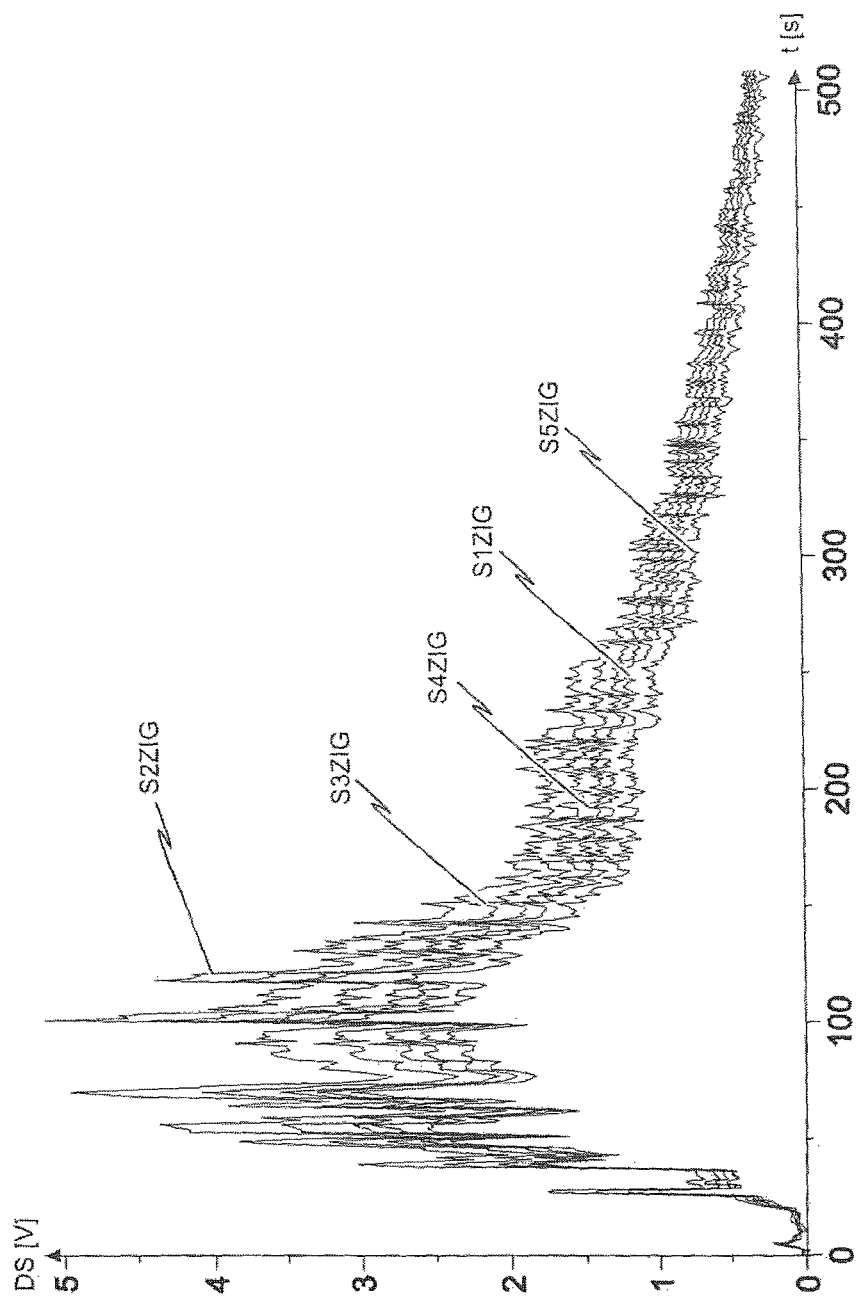
FIG. 8 are signal profiles analogous to FIG. 3 for a second test fire.
Figure 9:
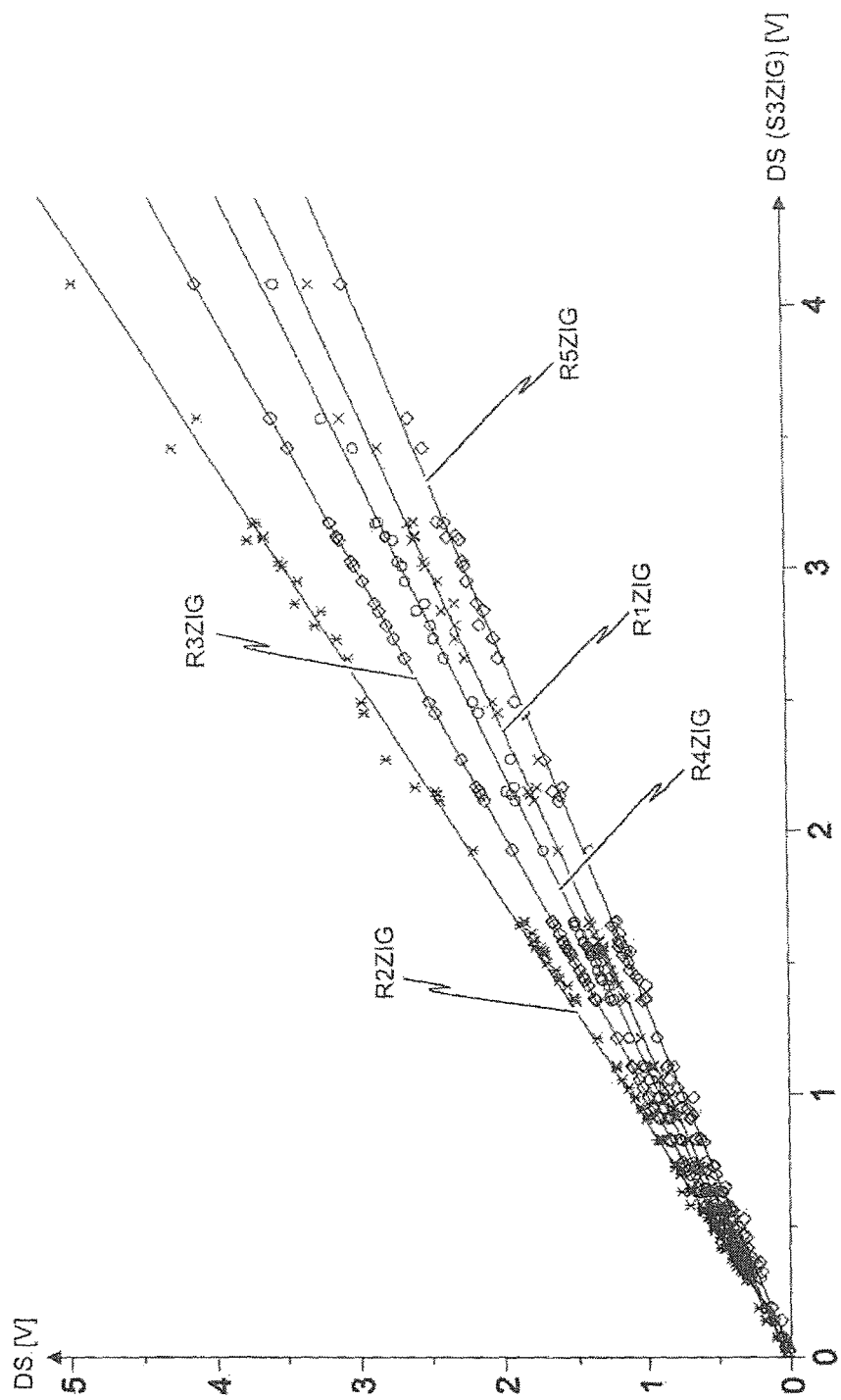
FIG. 9 regression lines analogous to FIG. 4 for the second test fire.
Figure 10:
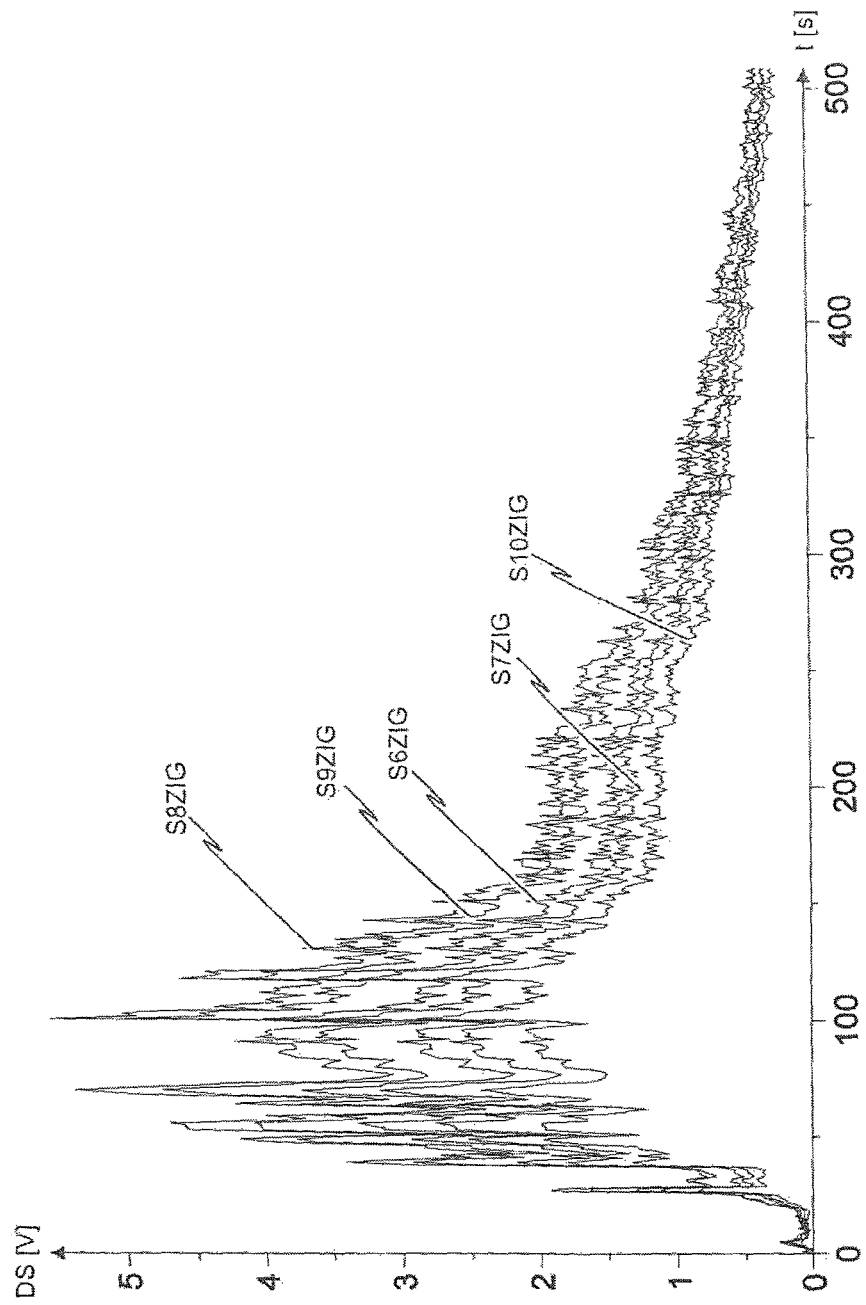
FIG. 10 are signal profiles analogous to FIG. 5 for the second test fire.
Figure 11:
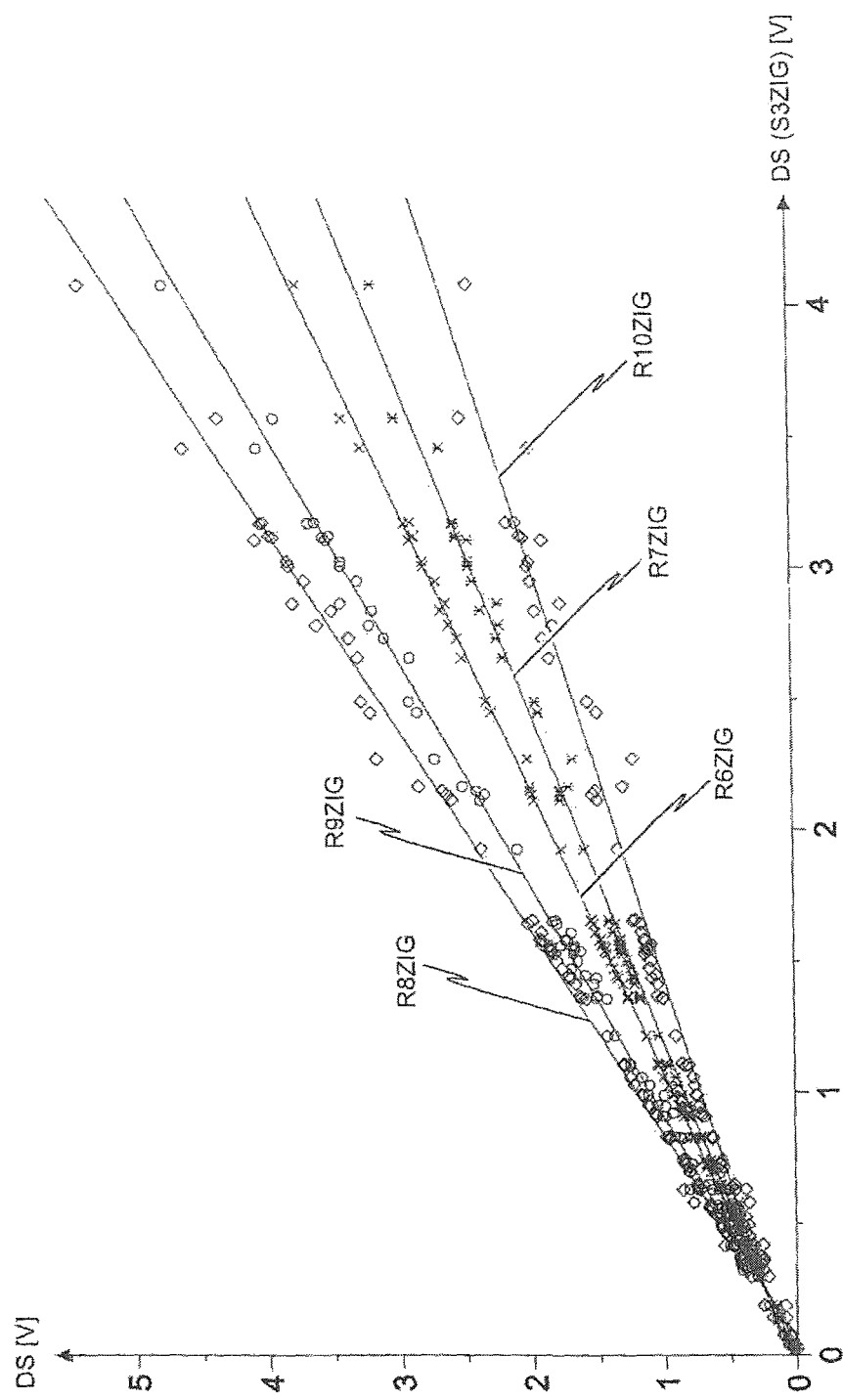
FIG. 11 are regression lines analogous to FIG. 6 for the second test fire.
Figure 12:
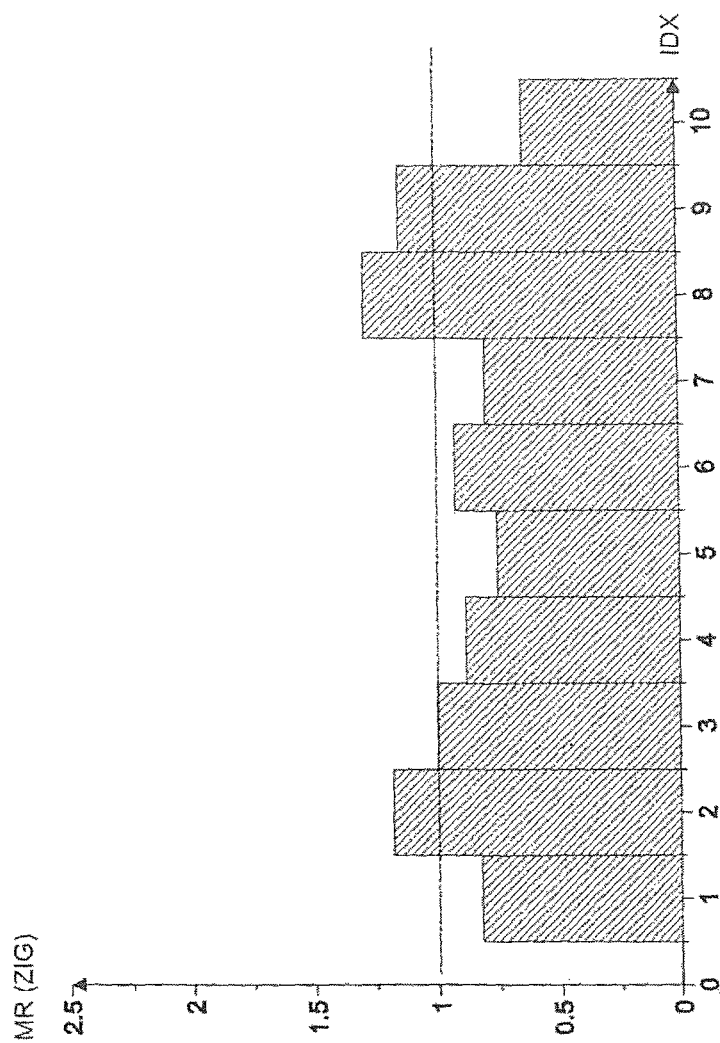
FIG. 12 are slopes of the best-fit lines analogous to FIG. 7 for the second test fire.
Figure 13:
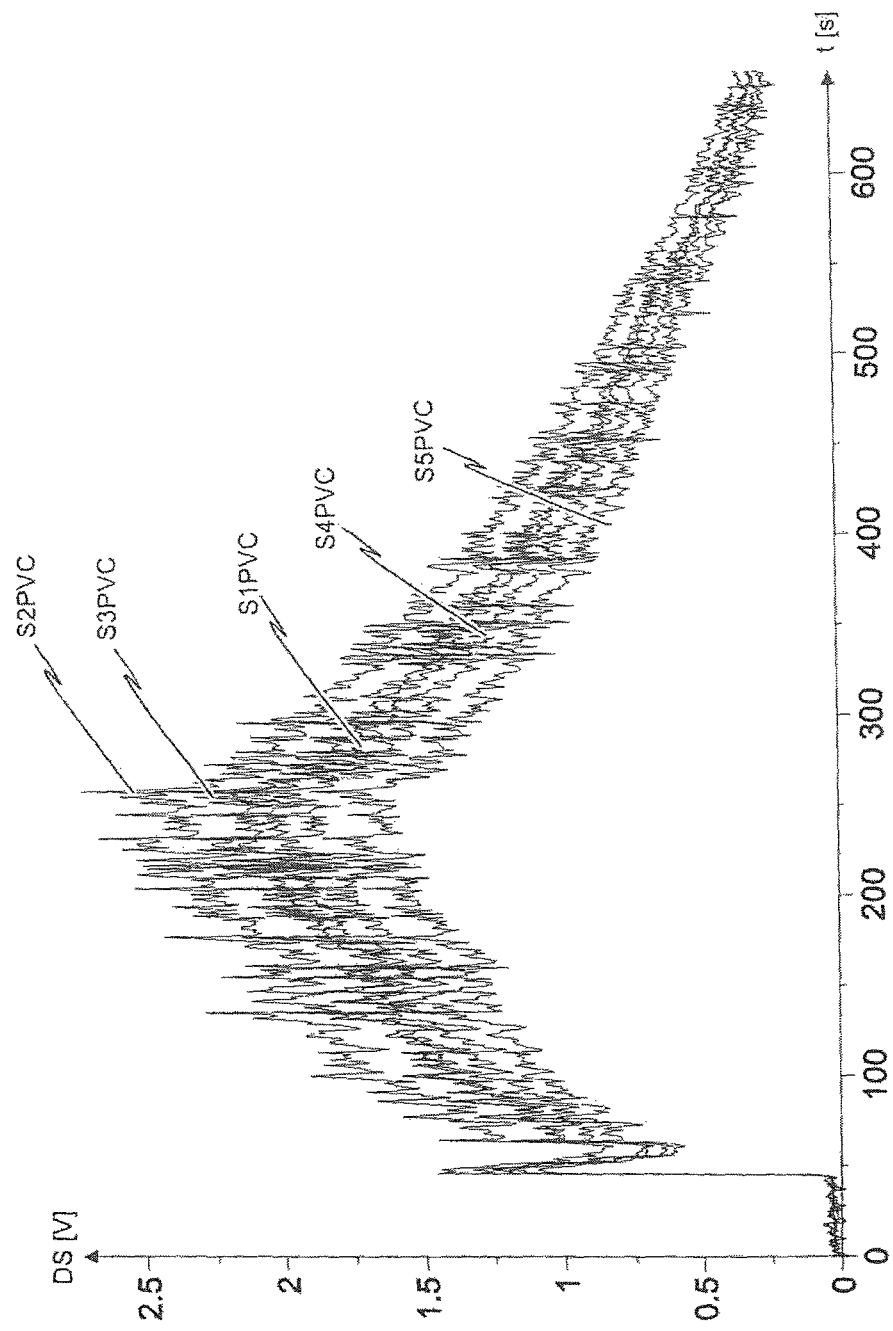
FIG. 13 are signal profiles analogous to FIG. 3 for a third test fire.

FIG. 7 lastly shown the associated distribution pattern of the regression lines from FIGS. 4 and 6 during the measurement of the scattered light as occurs during a paper fire. The slopes MR of the regression lines from FIGS. 4 and 6 are depicted in FIG. 7 as a bar chart across the sensor index IDX, whereby the sensor indices 1 to 10 correspond to optical sensors 21 to 30.

The pattern obtained in FIG. 7 is characteristic of the scattered light distribution during a paper fire and can be used for subsequent pattern matchings, particularly and preferably also automatic pattern matchings in a correspondingly designed evaluation unit. Particularly when a device having a reduced number of sensors according to the second embodiment from FIG. 2 is then also used during a later real measurement, the pattern distribution of FIG. 7 (with correctly assigned sensor indices IDX) can be utilized. It is thus established that, particularly with the specific sensor arrangement according to the second embodiment from FIG. 2, the sensor signals of the optical sensors 21, 23, 24 and 30, which correspond to sensor indices 1, 3, 4 and 10, suffice in classifying the type of fire at sufficiently high enough accuracy during the normalizing to the signal profile of the reference sensor 23 (sensor index 3).

FIGS. 8 to 12, and 13 to 17 respectively, depict signal patterns, their regression lines as well as their slope-related pattern distributions for a second test measurement (cigarette fire, ZIG) and a third test measurement (PVC fire PVC). Specifically, FIGS. 8/10 show the signal profiles from the second test measurement during a cigarette fire over a period of from 0 to approximately 500 seconds, separated in each case for the optical sensors 21, 22, 23, 24, 25 on the left in FIG. 1 and the optical sensors 26, 27, 28, 29, 30 on the right in FIG. 1 with the associated (left-side) regression lines in FIG. 9 and the (right-side) regression lines in FIG. 11. The regression is again carried out in relation to the sensor signal of optical sensor 23 serving as the reference sensor (signal profile S3 ZIG). Even just from a purely visual comparison, the characteristic pattern for a cigarette fire from FIG. 12 hereby clearly differs from the characteristic FIG. 7 pattern of a paper fire, which shows the good suitability of the inventive device for detecting scattered light signals where the signal profiles of the optical sensors serve in classifying the type of any particles which may be present in the scattered light area 15. It is in turn also apparent here that just the slope profiles for the reduced number of sensors according to the second embodiment from FIG. 2 (only sensor indices 1, 3, 4 and 10 are taken into account) suffice to be able to classify fire type at high accuracy.

Figure 14:
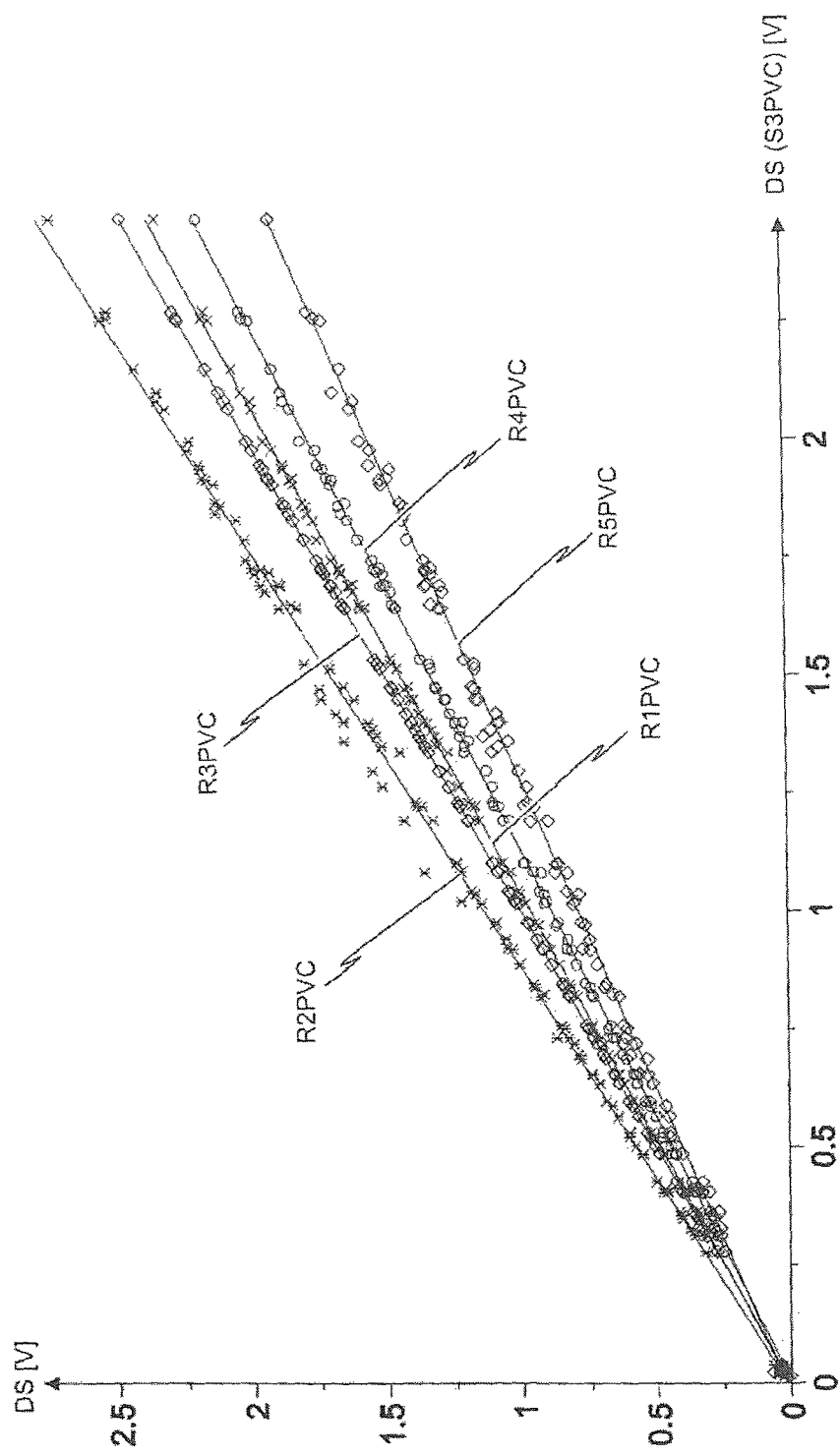
FIG. 14 are regression lines analogous to FIG. 4 for the third test fire.
Figure 15:
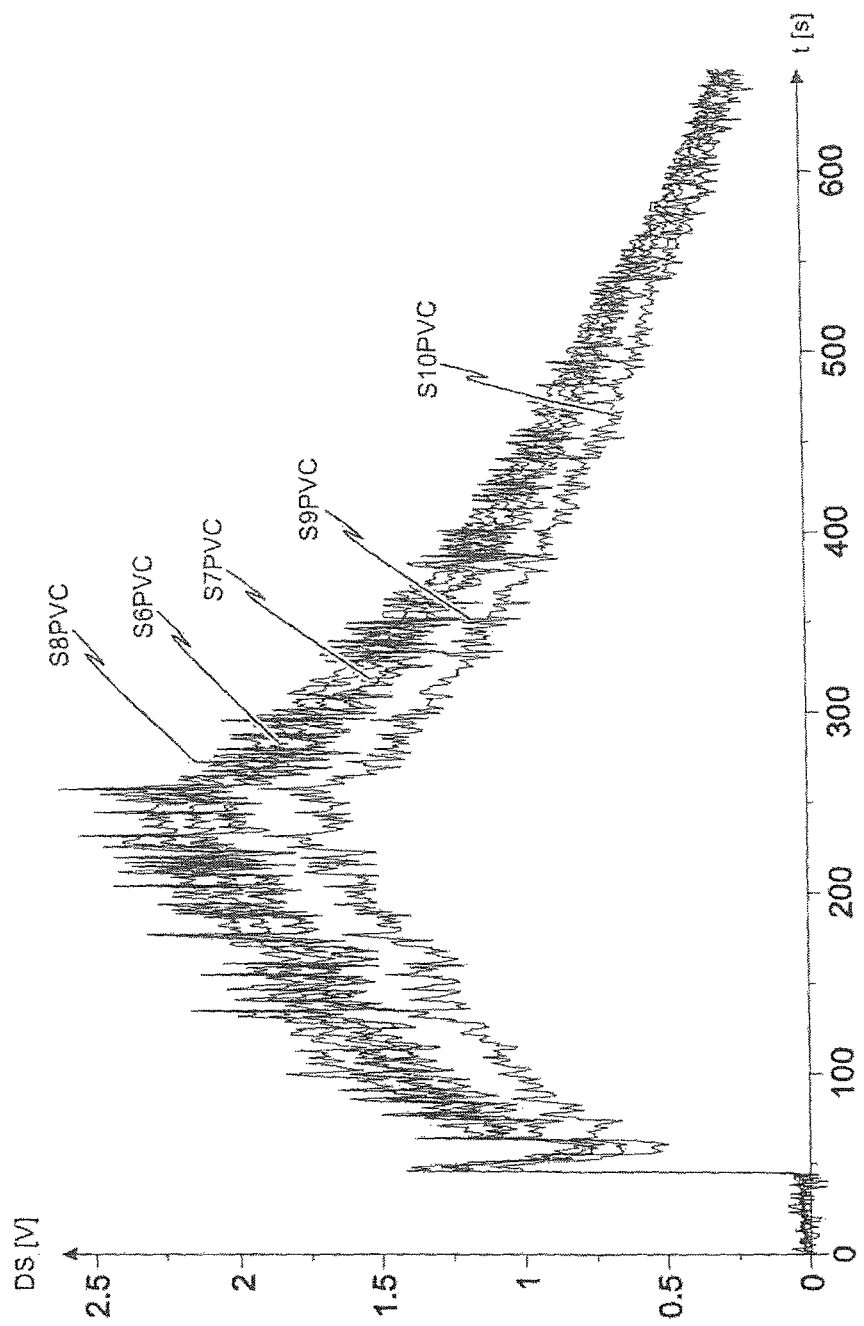
FIG. 15 are signal profiles analogous to FIG. 5 for the third test fire.
Figure 16:
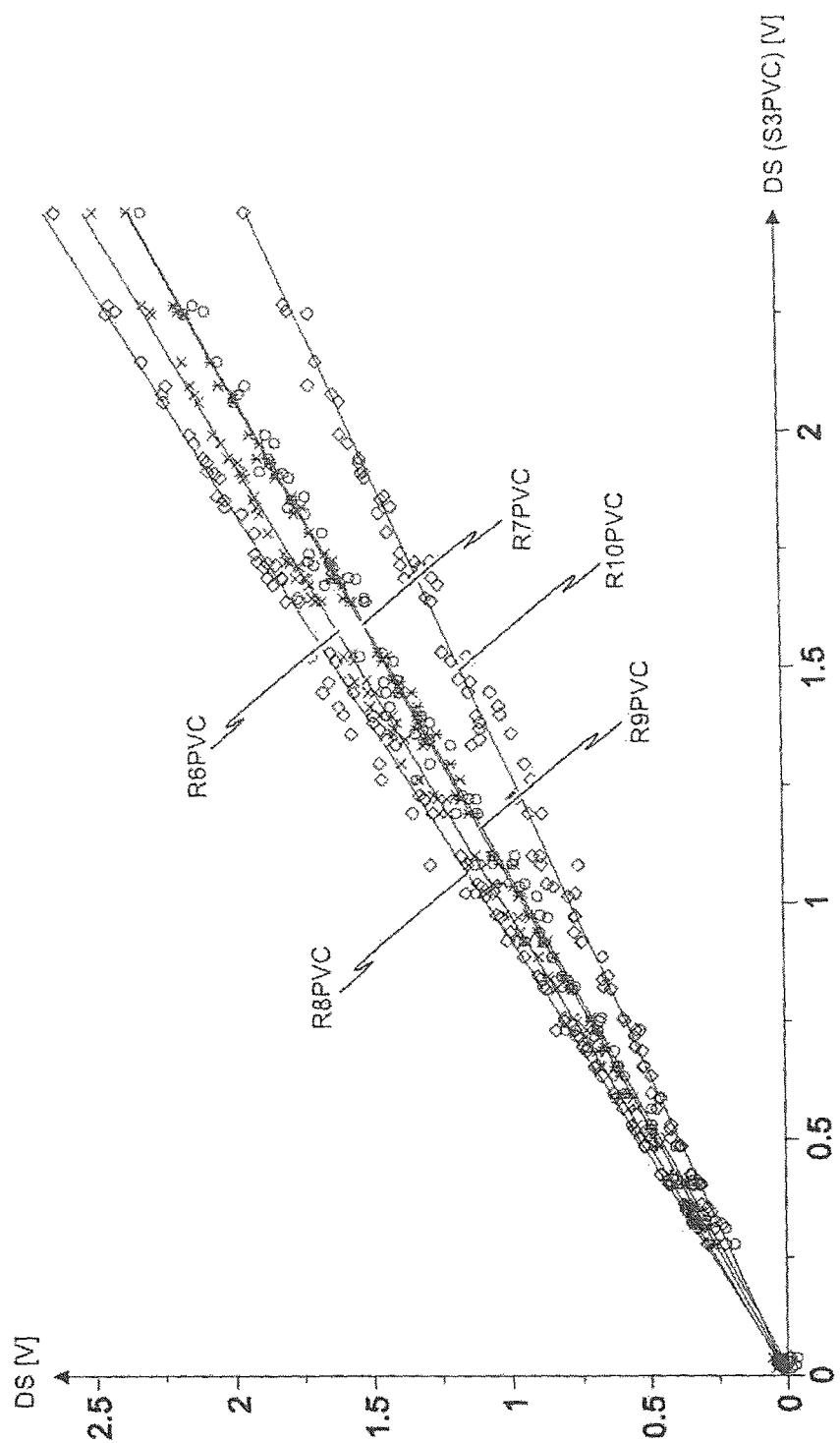
FIG. 16 are regression lines analogous to FIG. 6 for the third test fire.
Figure 17:
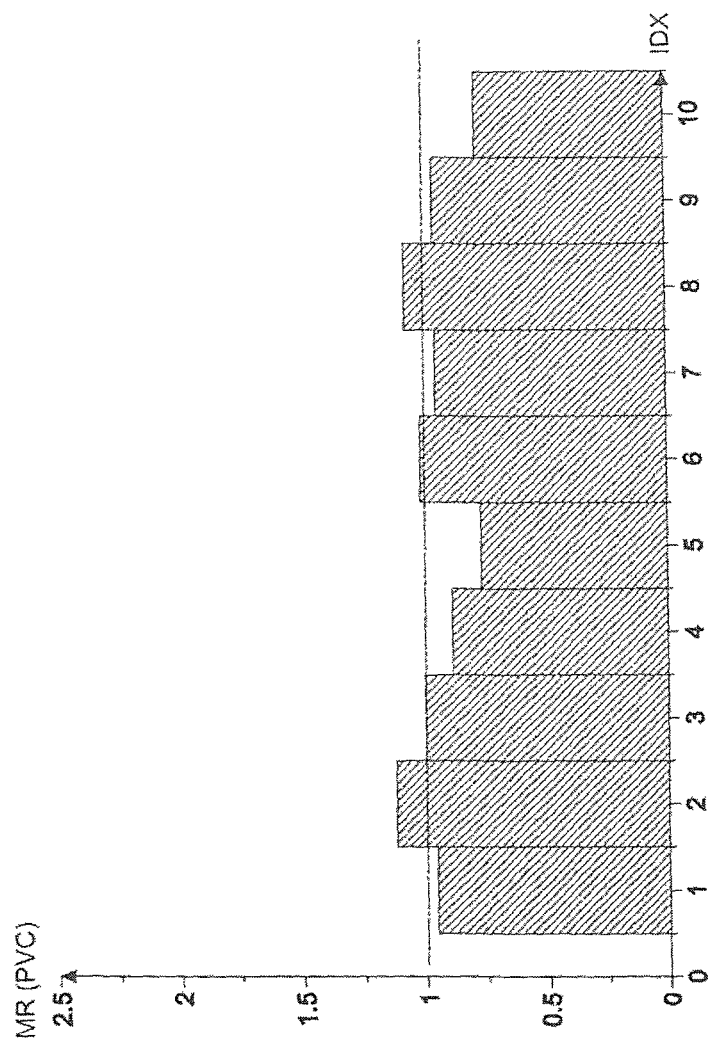
FIG. 17 are slopes of the best-fit lines analogous to FIG. 7 for the third test fire.

FIGS. 13 and 15 again show signal profiles of the left-side/right-side sensors from the test measurement during a PVC fire with their respective regression lines (again related to the detection signal of optical sensor 23 serving as the reference sensor) in FIGS. 14 and 16. Comparing the pattern of the slopes MR of the regression lines during a PVC fire as shown in FIG. 17 again shows, in comparison to FIGS. 7 and 12, the clearly different scattered light characteristics allowing high detection and classification accuracy.

Figure 18:
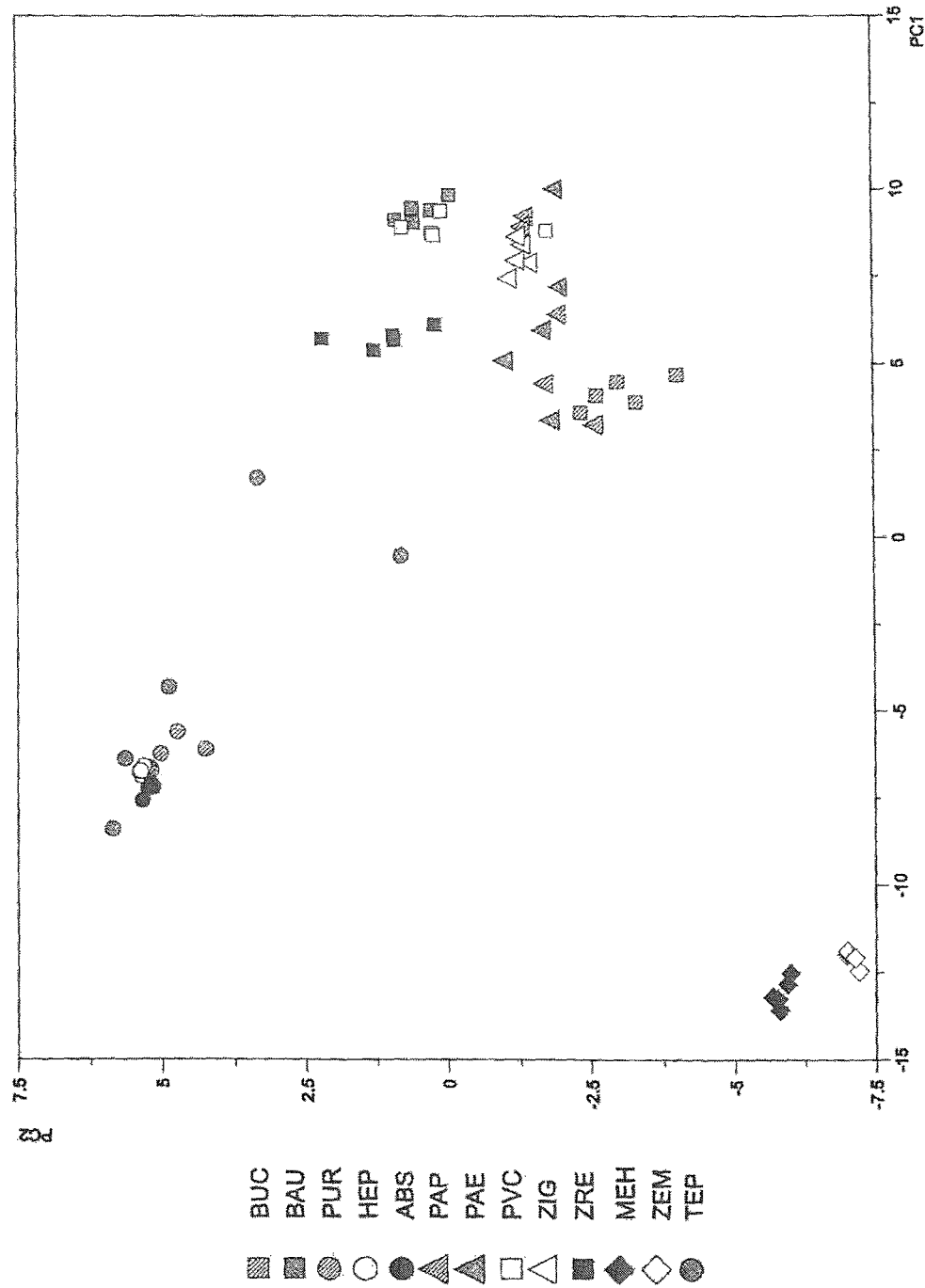
FIG. 18 is a depiction of the applicable cluster of sensor data for the implementation of a principal component analysis for different types of fire, principal component 2 (PC2) over principal component 1 (PC1)
Figure 19:
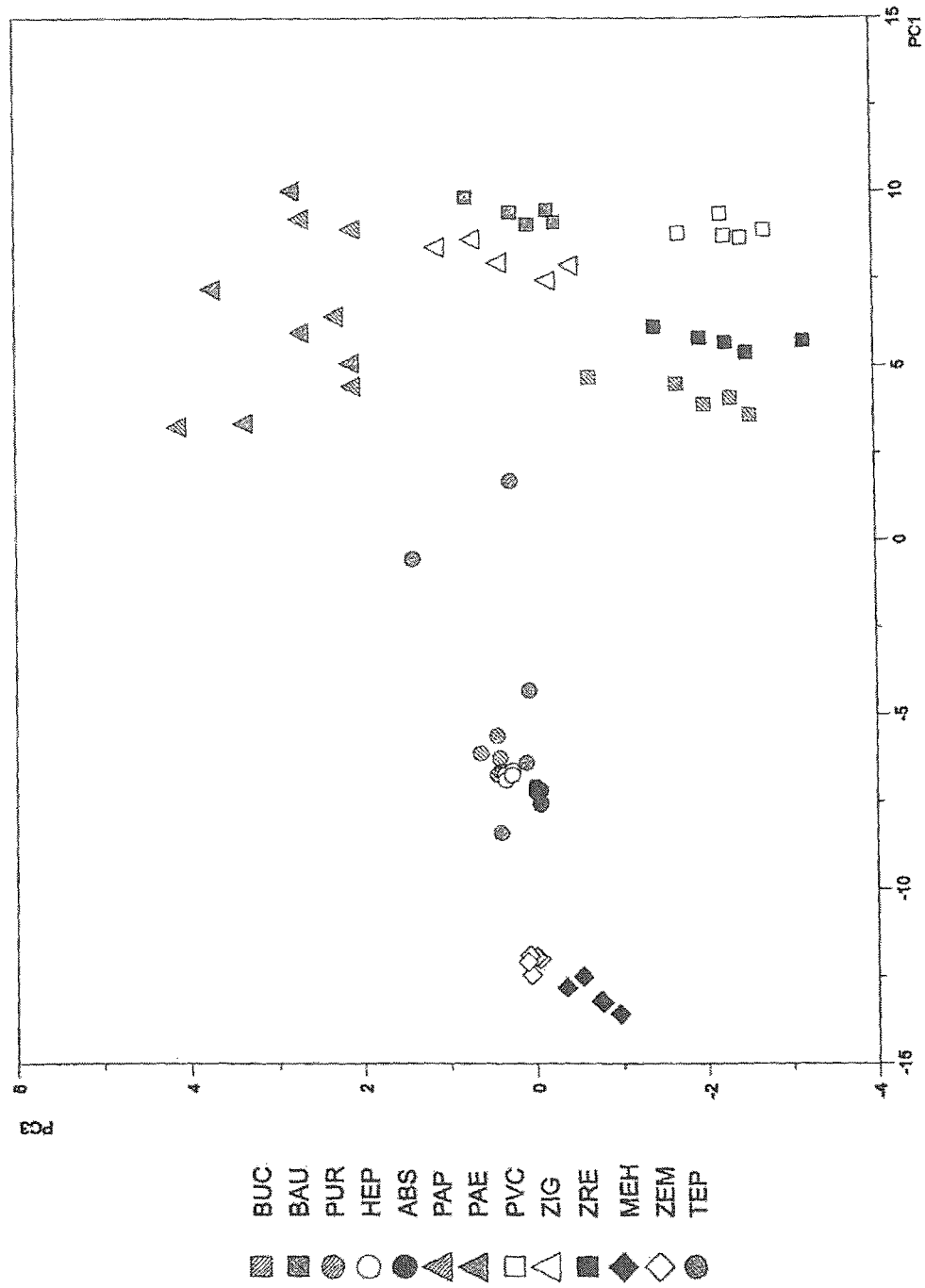
FIG. 19 is a cluster depiction analogous to FIG. 18 for a third principal component (PC3) over the first principal component (PC1)
Figure 20:
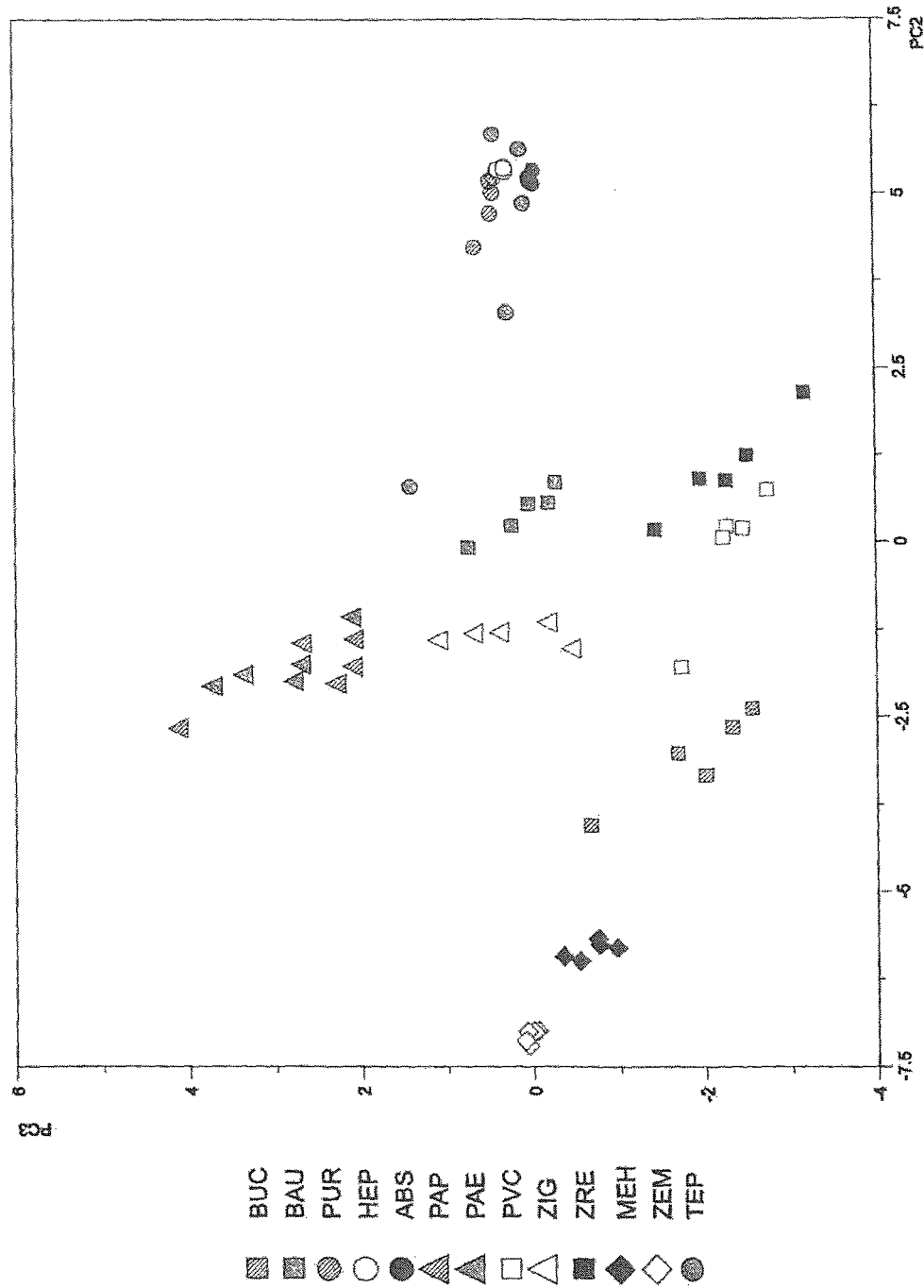
FIG. 20 is a cluster depiction analogous to FIGS. 18 and 19 for the third principal component (PC3) over the second principal component (PC2).

FIGS. 18 to 20 clarify a further possible application of the measuring signals distinct from the regression lines using a principal component analysis (PCA).

Utilizing a principal component analysis is particularly advantageous in the present case since a parametric approach would require a complicated and CPU-intensive discerning of the structure of the mathematical system of light source and scattered light sensors. Principal component analysis (PCA) allows dimensional reduction based solely on statistical methods.

FIGS. 18 to 20 depict individual clusters BUC, BAU, PUR, HEP, ABS, PAP, PAE, PVC, ZIG, ZRE, MEH, ZEM, TEP of pattern signal profiles pursuant a principal component analysis reduced to three principal components PC1, PC2, PC3, whereby FIG. 18 depicts principal component 2 (PC2) against principal component 1 (PC1), FIG. 19 depicts principal component 3 (PC3) against principal component 1 (PC1) and FIG. 20 depicts principal component 3 (PC3) against principal component 2 (PC2). The individual BUC, BAU, PUR, HEP, ABS, PAP, PAE, PVC, ZIG, ZRE, MEH, ZEM, TEP clusters hereby correspond to the characteristics of the following types of fire:

| Cluster | Fire type |
| --- | --- |
| BUC | Beechwood |
| BAU | cotton |
| PUR | PUR |
| HEP | n-heptane |

| Cluster | Fire type |
|---------|-----------|
| ABS | ABS |
| PAP | paper |
| PAE | cardboard |
| PVC | PVC |
| ZIG | cigarette |
| ZRE | cigar |
| MEH | flour dust |
| ZEM | cement dust |
| TEP | carpet |

When measurements of actual fires are taken with the device according to the invention for detecting scattered light signals, evaluation is made based on the clusters from FIGS. 18 to 20 using principal component analysis with a distance determination of the signal profile distribution of the detected signals (measured cluster) obtained pursuant principal component analysis to clusters of the signal pattern from FIGS. 18 to 20 (pattern clusters).

The principal component analysis hereby provides the advantage of a relatively simple dimensional reduction with the thereby associated advantageous noise reduction, wherein essentially only the signal components relevant to fire or particle classification respectively are taken into account.

It is pointed out here that all the elements described above alone and in any combination, particularly the specifics portrayed in the drawings, are claimed as being essential to the invention, modifications of which will be familiar to one skilled in the art.

LIST OF REFERENCE NUMERALS

10 light source
11 incident axis
15 scattered light area
16 detection region
21, 22, 23, 24, 25, 26, 27, 28, 29, 30 optical sensor
41, 42, 43, 44, 45, 46, 47, 48, 49, 50 polarizing filter
100 device for detecting scattered light signals
DS detection signal
S1PAP, S2PAP, S3PAP, S4PAP S5PAP, S6PAP, S7PAP, S8PAP, S9PAP, S10PAP, S1ZIG, S2ZIG, S3ZIG, S4ZIG, S5ZIG, S6ZIG, S7SIG, S8ZIG, S9ZIG, S10ZIG, S1PVC, S2PVC, S3PVC, S4PVC, S5PVC, S6PVC, S7PVC, S8PVC S9PVC, S10PVC sensor signals
R1PAP, R2PAP, R3PAP, R4PAP, R5PAP, R6PAP, R7PAP, R8PAP, R9PAP, R10PAP, R1ZIG, R2ZIG, R3ZIG, R4ZIG, R5ZIG, R6ZIG, R7ZIG, R8ZIG, R9ZIG, R10ZIG, R1PVC, R2PVC, R3PVC, R4PVC, R5PVC, R6PVC, R7PVC, R8PVC, R9PVC R10PVC regression profiles
MR regression profile slope
IDX sensor index
BUC, BAU, PUR, HEP, ABS, PAR, PAE, PVC, ZIG, ZRG, MEH, ZEM, TEP signal profile cluster
W1, W2, W3, W4, W5, W6, W7, W8, W9, W10 sensor angle

What is claimed is:

1. A device for detecting scattered light signals, the device comprising:
   a light source configured to emit light in a scattered light area where incident light of the emitted light defines an incident axis;
   a plurality of optical sensors each arranged at a sensor angle relative to the incident axis and configured to detect scattered light from the scattered light area and where at least one of the plurality of optical sensors is a reference sensor; and
   an evaluation unit configured to evaluate signals detected by the optical sensors to obtain signal profiles associated with the optical sensors, the evaluation unit relating the signal profiles of the other optical sensors to the signal profile of the at least one reference sensor to classify a type on any particle in the scattered light area.

2. The device according to claim 1, wherein the evaluation unit is further configured to:
   distinguish automatically between a fire parameter and a false variable as a function of the classified particle type.

3. The device according to claim 1, further comprising:
   an alarming device configured to emit an alarm as a function of the classified particle type.

4. The device according to claim 3, wherein one or more particle types for which the alarming device will issue an alarm is predefined or predefinable.

5. The device according to claim 3, wherein the alarming device is further configured to:
   emit the alarm independent of a threshold.

6. The device according to claim 3, wherein the alarming device is further configured to:
   emit different signals, that include at least particular types of alarms and all-clear signals, as a function of the classified particle type.

7. The device according to claim 1, wherein the at least one reference sensor is arranged at a substantially right sensor angle.

8. The device according to claim 1, wherein the evaluation device is further configured to:
   compare data obtained from the signal profiles of the signals detected from the plurality of optical sensors to signal patterns to classify a particular particle in the scattered light area as a particle type, and emit an identification signal identifying the classified particle type upon a threshold degree of correspondence to a signal pattern.

9. The device according to claim 1, wherein the evaluation device is further configured to determine a particle level as a function of an intensity of the scattered light detected by the at least one reference sensor.

10. The device according to claim 9, wherein the evaluation device is further configured to not perform pattern matching until the particle level exceeds a minimum particle level.

11. The device according to claim 1, wherein the light source is configured to emit substantially monochromatic light in a wavelength range of approximately 560 to approximately 420 nanometers.

12. The device according to claim 1, wherein at least one of the plurality of optical sensors includes a polarizing filter for polarizing the scattered light to be detected.

13. The device according to claim 12, wherein a first set of the plurality of optical sensors include the polarizing filter, wherein polarization planes of at least two polarizing filters are arranged substantially perpendicular to each other.

14. The device according to claim 12, wherein each of the plurality of optical sensors includes a polarizing filter, wherein polarization planes of at least two polarizing filters are arranged substantially perpendicular to each other.

15. The device according to claim 1, wherein each of the plurality of optical sensors is substantially aligned toward a common detection region of the scattered light area.

16. The device according to claim 1, wherein at least one of the plurality of optical sensors is designed as a photodiode and wherein the light source is a light-emitting diode.

17. The device according to claim 1, wherein the plurality of optical sensors includes a first optical sensor at a first sensor angle, a second optical sensor at a second sensor angle, a third optical sensor at a third sensor angle, and wherein the first sensor angle is an acute angle and totals 360° together with the second sensor angle, and wherein the third sensor angle is an obtuse angle.

18. The device according to claim 17, wherein the first sensor angle amounts to approximately 45° and the second sensor angle amounts to approximately 315°, and wherein the third sensor angle amounts to approximately 112°.

19. The device according to claim 17, wherein the at least one reference sensor, the first optical sensor at the first sensor angle, the second optical sensor at the second sensor angle and the third optical sensor at the third sensor angle each include a polarizing filter, and wherein the polarizing filters of the reference sensor, the first optical sensor at the first sensor angle and the third optical sensor at the third sensor angle are aligned with one another in a first polarization plane, and wherein the polarizing filter of the second optical sensor at the second sensor angle is aligned in a second polarization plane perpendicular to the first polarization plane.

20. The device according to claim 1, wherein the evaluation device is further configured to determine a degree of correspondence by correlating data obtained from distribution of the signal profiles of the detected signals according to a principal component analysis into clusters of signal patterns.

21. The device according to claim 1, wherein the evaluation device is further configured to determine a degree of correspondence by distance determination of data obtained from distribution of the signal profiles of the detected signals according to a principal component analysis into clusters of signal patterns.

22. The device according to claim 1, wherein the evaluation device is further configured to determine a degree of correspondence by neuronal network evaluation of data obtained from distribution of the signal profiles of the detected signals according to a principal component analysis into clusters of signal patterns.

23. The device according to claim 20, wherein the signal patterns correspond to particle distribution signals of one or more particle emissions selected from the group consisting of: dust emission, vapor emission, tobacco smoke emission, smoldering paper fire, smoldering cardboard fire, open paper fire, open cardboard fire, ABS fire, n-heptane fire, PVC fire, cotton fire, wood fire, and other particle emissions.

24. The device according to claim 1, wherein the device is used in an aspirative fire detection system, wherein the aspirative fire detection system includes an active air supply for supplying air to be classified in the scattered light area.

25. The device according to claim 1, further comprising:
an inertization system configured to selectively control reduction of oxygen content in an enclosed room and for maintaining reduced oxygen content over a defined period of time, wherein the inertization system sets oxygen content as a function of a control signal based on detecting scattered light signals.

26. The device according to claim 25, wherein the control signal is the identification signal identifying the classified particle and the inertization system is configured to automatically set the reduced oxygen content and maintain it over the defined period of time.

27. A method for detecting scattered light signals, the method comprising:
supplying light in a scattered light area, wherein incident light from the supplied light defines an incident axis;
detecting, by a plurality of optical sensors, scattered light which reflects on a particle present in the scattered light area, each of the plurality of optical sensors arranged at a sensor angle relative to the incident axis and at least one of the plurality of optical sensors being a reference sensor;
relating signal profiles of the other optical sensors to a signal profile of the at least one reference sensor; and
classifying the particle present in the scattered light area as a type of particle based on relating the signal profiles of the other optical sensors to the signal profile of the at least one reference sensor.

28. The method according to claim 27, further comprising:
determining a particle level as a function of an intensity of the scattered light detected by the reference sensor.

29. The method according to claim 27, further comprising:
comparing data obtained from the signal profiles of the signals detected from the plurality of optical sensors to signal patterns to classify the particle as the type; and
emitting an identification signal to an inertization system for selectively automatic controlled reduction of oxygen content in an enclosed room, wherein the identification signal identifies the type of particle classified.

* * * * *